(12) United States Patent
Case et al.

(10) Patent No.: US 8,128,682 B2
(45) Date of Patent: Mar. 6, 2012

(54) MEDICAL DEVICE WITH TENSIONABLY ATTACHED REMODELABLE MATERIAL

(75) Inventors: Brian C. Case, Bloomington, IN (US); Jacob A. Flagle, Indianapolis, IN (US); Ram H. Paul, Jr., Bloomington, IN (US); Sean D. Chambers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 122 days.

(21) Appl. No.: 12/777,947

(22) Filed: May 11, 2010

(65) Prior Publication Data

US 2010/0280586 A1    Nov. 4, 2010

Related U.S. Application Data

(63) Continuation of application No. 11/435,508, filed on May 17, 2006, now abandoned, which is a continuation-in-part of application No. 11/103,137, filed on Apr. 11, 2005, now Pat. No. 7,582,110.

(60) Provisional application No. 60/681,863, filed on May 17, 2005.

(51) Int. Cl.
*A61F 2/82* (2006.01)

(52) U.S. Cl. .................. 623/1.24; 623/1.13; 623/1.3

(58) Field of Classification Search ................ 623/1.24, 623/1.13, 1.15; *A61F 2/06*
See application file for complete search history.

(56) References Cited

U.S. PATENT DOCUMENTS

| | | | |
|---|---|---|---|
| 3,063,967 A | 11/1962 | Schultz | |
| 3,063,968 A | 11/1962 | Schultz | |
| 3,169,945 A | 2/1965 | Hostettler et al. | |
| 3,391,126 A | 7/1968 | Baggett et al. | |
| 3,645,941 A | 2/1972 | Snapp et al. | |
| 3,912,692 A | 10/1975 | Casey et al. | |
| 3,942,532 A | 3/1976 | Hunter et al. | |
| 4,052,988 A | 10/1977 | Doddi et al. | |
| 4,076,807 A | 2/1978 | Trinh et al. | |
| 4,243,775 A | 1/1981 | Rosensaft et al. | |
| 4,300,565 A | 11/1981 | Rosensaft et al. | |

(Continued)

FOREIGN PATENT DOCUMENTS

DE    10223399    12/2003

(Continued)

OTHER PUBLICATIONS

D.K. Gilding, A.M. Reed, "Biodegradable polymers for use in surgery—polyglycolic/poly(actic acid) homo- and copolymers: 1," Polymer, 1997, vol. 20, 1459-1464.

(Continued)

*Primary Examiner* — Thomas J Sweet
*Assistant Examiner* — Jason-Dennis Stewart
(74) *Attorney, Agent, or Firm* — Buchanan Nipper

(57) ABSTRACT

Medical devices for implantation in a body vessel, and methods of using and making the same, are provided. A medical device includes a support frame having struts and a weakened frame portion, and a remodelable material tensionably attached to the support frame. The weakened frame portion has a first configuration in which the support frame has a first outward radial force and a second configuration in which the support frame has a second, lesser outward radial force. The remodelable material restricts expansion of the frame from a radially compressed configuration to a radially expanded configuration when the weakened frame portion is in the first configuration. The remodelable material can form one or more valve leaflets adapted to regulate fluid flow in a body vessel, such as a vein.

20 Claims, 10 Drawing Sheets

U.S. PATENT DOCUMENTS

| | | |
|---|---|---|
| 4,429,080 A | 1/1984 | Casey et al. |
| 4,440,789 A | 4/1984 | Mattei et al. |
| 4,549,921 A | 10/1985 | Wolfe, Jr. |
| 4,559,945 A | 12/1985 | Koelmel et al. |
| 4,591,630 A | 5/1986 | Gertzman et al. |
| 4,605,730 A | 8/1986 | Shalaby et al. |
| 4,624,256 A | 11/1986 | Messier et al. |
| 4,643,191 A | 2/1987 | Bezwada et al. |
| 4,643,734 A | 2/1987 | Lin |
| 4,653,497 A | 3/1987 | Bezwada et al. |
| 4,700,704 A | 10/1987 | Jamiolkowski et al. |
| 4,776,337 A | 10/1988 | Palmaz |
| 4,788,979 A | 12/1988 | Jarrett et al. |
| 4,791,929 A | 12/1988 | Jarrett et al. |
| 4,816,028 A | 3/1989 | Kapadia et al. |
| 4,838,267 A | 6/1989 | Jamiolkowski et al. |
| 4,856,516 A | 8/1989 | Hillstead |
| 4,893,623 A | 1/1990 | Rosenbluth |
| 4,969,458 A | 11/1990 | Wiktor |
| 4,994,071 A | 2/1991 | MacGregor |
| 4,994,074 A | 2/1991 | Bezwada et al. |
| 5,007,923 A | 4/1991 | Bezwada et al. |
| 5,019,085 A | 5/1991 | Hillstead |
| 5,047,048 A | 9/1991 | Bezwada et al. |
| 5,067,491 A | 11/1991 | Taylor, II et al. |
| 5,076,807 A | 12/1991 | Bezwada et al. |
| 5,080,665 A | 1/1992 | Jarrett et al. |
| 5,085,629 A | 2/1992 | Goldberg et al. |
| 5,100,433 A | 3/1992 | Bezwada et al. |
| 5,104,404 A | 4/1992 | Wolff |
| 5,116,365 A | 5/1992 | Hillstead |
| 5,133,755 A | 7/1992 | Brekke |
| 5,135,536 A | 8/1992 | Hillstead |
| 5,174,295 A | 12/1992 | Christian et al. |
| 5,178,618 A | 1/1993 | Kandarpa |
| 5,234,457 A | 8/1993 | Andersen |
| 5,282,824 A | 2/1994 | Gianturco |
| 5,293,879 A | 3/1994 | Vonk et al. |
| 5,314,472 A | 5/1994 | Fontaine |
| 5,342,387 A | 8/1994 | Summers |
| 5,366,473 A | 11/1994 | Winston et al. |
| 5,380,320 A | 1/1995 | Morris |
| 5,383,892 A | 1/1995 | Cardon et al. |
| 5,389,106 A | 2/1995 | Tower |
| 5,393,594 A | 2/1995 | Koyfman et al. |
| 5,412,068 A | 5/1995 | Tang et al. |
| 5,421,955 A | 6/1995 | Lau et al. |
| 5,443,496 A | 8/1995 | Schwartz |
| 5,449,373 A | 9/1995 | Pinchasik |
| 5,468,253 A | 11/1995 | Bezwada et al. |
| 5,507,767 A | 4/1996 | Maeda et al. |
| 5,514,154 A | 5/1996 | Lau et al. |
| 5,522,841 A | 6/1996 | Roby et al. |
| 5,527,354 A | 6/1996 | Fontaine et al. |
| 5,540,712 A | 7/1996 | Kleshinski et al. |
| 5,540,713 A | 7/1996 | Schnepp-Pesch et al. |
| 5,549,662 A | 8/1996 | Fordenbacher |
| 5,549,663 A | 8/1996 | Cottone, Jr. |
| 5,554,181 A | 9/1996 | Das |
| 5,591,197 A | 1/1997 | Orth et al. |
| 5,591,198 A | 1/1997 | Boyle et al. |
| 5,607,442 A | 3/1997 | Fischell et al. |
| 5,607,445 A | 3/1997 | Summers |
| 5,613,981 A | 3/1997 | Boyle et al. |
| 5,624,449 A | 4/1997 | Pham et al. |
| 5,630,829 A | 5/1997 | Lauterjung |
| 5,636,641 A | 6/1997 | Fariabi |
| 5,643,312 A | 7/1997 | Fischell et al. |
| 5,653,727 A | 8/1997 | Wiktor |
| 5,681,346 A | 10/1997 | Orth et al. |
| 5,697,971 A | 12/1997 | Fischell et al. |
| 5,705,181 A | 1/1998 | Cooper et al. |
| 5,713,920 A | 2/1998 | Bezwada et al. |
| 5,725,572 A | 3/1998 | Lam et al. |
| 5,728,158 A | 3/1998 | Lau et al. |
| 5,733,303 A | 3/1998 | Israel et al. |
| 5,735,893 A | 4/1998 | Lau et al. |
| 5,741,327 A | 4/1998 | Frantzen |
| 5,749,919 A | 5/1998 | Blanc |
| 5,755,776 A | 5/1998 | Al-Saadon |
| 5,759,192 A | 6/1998 | Saunders |
| 5,766,238 A | 6/1998 | Lau et al. |
| 5,776,161 A | 7/1998 | Globerman |
| 5,807,404 A | 9/1998 | Richter |
| 5,855,600 A | 1/1999 | Alt |
| 5,891,128 A | 4/1999 | Gia et al. |
| 5,895,420 A | 4/1999 | Mirsch, II et al. |
| 5,935,148 A | 8/1999 | Villar et al. |
| 5,944,733 A | 8/1999 | Engelson |
| 6,059,779 A | 5/2000 | Mills |
| 6,090,127 A | 7/2000 | Globerman |
| 6,287,332 B1 | 9/2001 | Bolz et al. |
| 6,287,336 B1 | 9/2001 | Globerman et al. |
| 6,425,914 B1 | 7/2002 | Wallace et al. |
| 6,428,570 B1 | 8/2002 | Globerman |
| 6,553,801 B2 | 4/2003 | Chen |
| 6,589,230 B2 | 7/2003 | Gia et al. |
| 6,602,286 B1 | 8/2003 | Strecker |
| 6,656,216 B1 | 12/2003 | Hossainy et al. |
| 7,163,556 B2 | 1/2007 | Xie et al. |
| 7,273,492 B2 | 9/2007 | Cheng et al. |
| 7,582,110 B2 | 9/2009 | Case et al. |
| 2001/0039450 A1 | 11/2001 | Pavcnik et al. |
| 2001/0041930 A1 | 11/2001 | Globerman et al. |
| 2003/0153972 A1 | 8/2003 | Helmus |
| 2004/0167619 A1 | 8/2004 | Case et al. |
| 2004/0210301 A1 | 10/2004 | Obermiller |
| 2005/0038501 A1 | 2/2005 | Moore et al. |
| 2005/0137681 A1 | 6/2005 | Shoemaker et al. |
| 2006/0276882 A1 | 12/2006 | Case et al. |
| 2007/0185560 A1 | 8/2007 | Roeder et al. |

FOREIGN PATENT DOCUMENTS

| | | |
|---|---|---|
| EP | 460428 | 12/1991 |
| EP | 0493788 | 7/1992 |
| EP | 0800801 | 10/1997 |
| WO | WO9721399 | 6/1997 |
| WO | WO9725937 | 7/1997 |
| WO | WO9732543 | 9/1997 |
| WO | WO9818404 | 5/1998 |
| WO | WO03063733 | 8/2003 |
| WO | WO03088872 | 10/2003 |

OTHER PUBLICATIONS

D.K. Gilding, "Biodegradable Polymers," Biocompatibility of Clinical Implant Materials, Chap. 9, pp. 209-232, 1981.

Gabriel Helmlinger, Bradford C. Berk, Robert M. Nerem, "Calcium responses of endothelial cell monolayers subjected to pulsatile and steady laminar flow differ," Am. J. Physiol. Cell Physiol., 269: C367-C375, 1995.

Matthias Chiquet, Mark Matthisson, Manuel Koch, Michael Tannheimer, Ruth Chiquet-Ehrismann, "Regulation of extracellular matrix synthesis by mechanical stress," Biochem. Cell Biol. 74, 737-744 (1996).

Yi-Shuan Li, John Y.-J Shyy, Song Li, Jongdae Lee, Bing US, Michael Karin, Shu Chien, "The Ras-JNK Pathway Is Involved in Shear-Induced Gene Expression," Molecular and Cellular Biology, 1996, 5947-5954.

Dana E. Perrin, James P. English, "Polycaprolactone," Handbook of Bioabsorbable Polymers, 1997, 63-76.

Wai Hung Wong, David J. Mooney, "Synthesis and Properties of Biodegradable Polymers Used as Synthetic Matrices for Tissue Engineering," I synthetic Biodegradable Polymer Scaffolds, 1997, 51-82.

Shu Chien, Song Li, John Y-J Shyy, "Effects of Mechanical Forces on Signal Transdution and Gene Expression in Endothelial Cells," Hypertension 31, 162-169, 1998.

Lamba, et al., "Degradation of Polyurethanes," Polyurethanes in Biomedical Applications, 181-204, 1998.

Matthias Chiquet, "Regulation of extracellular matrix gene expression by mechanical stress," Matrix Biol., 417-426, 1999.

Marcy Wong, Mark Siegrist, Xuesong Cao, "Cyclic compression of articular cartilage explants is associated with progressive consolidation and altered expression pattern of extracellular matrix proteins," Matrix Biology, 391-399, 1999.

Alan J. Grodzinsky, Marc E. Levenston, Moonsoo Jin, Eliot H. Frank, "Cartilage Tissue Remodeling in Response to Mechanical Forces," Annual Review of Biomedical Engineering, 691-713, 2000.

V.C. Mudera, R. Pleass, M. Eastwood, R. Tarnuzzer, G. Schultz, P. Khaw, D.A. McGrouther, R.A. Brown, "Molecular Responses of Human Dermal Fibroblasts to Dual Cues: Contact Guidance and Mechanical Load," Cell Motility and the Cytoskeleton, 45: 1-9, 2000.

Christof Schild, Beat Trueb, "Mechanical Stress is Required for High-Level Expression of Connective Tissue Growth Factor," Experimental Cell Research, 274: 83-91, 2002.

European Patent Office, International Preliminary Report on Patentability, May 30, 2006, for International application No. PCT/US2005012421.

European Patent Office, Written Opinion of the International Searching Authority, Oct. 13, 2006, for International application No. PCT/US2005/012421.

European Patent Office, Later Publication of the International Search Report, Jul. 8, 2005 for International application No. PCT/US2005/012421.

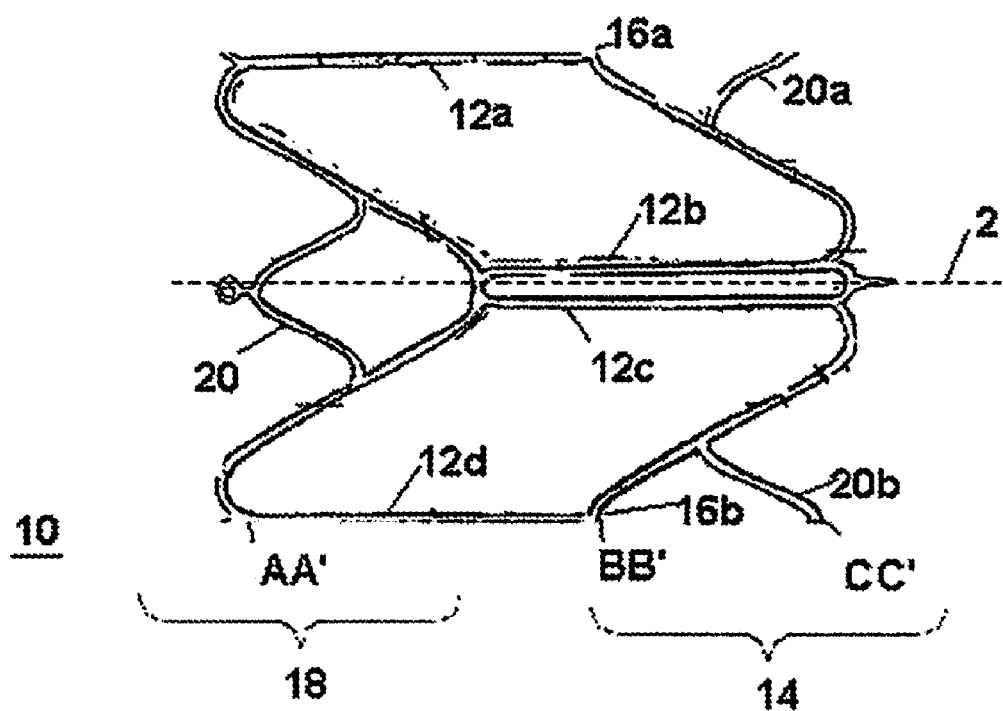

MEDICAL DEVICE WITH TENSIONABLY ATTACHED REMODELABLE MATERIAL

CROSS REFERENCE TO RELATED APPLICATIONS

This application is a continuation of co-pending U.S. patent application Ser. No. 11/435,508, filed on May 17, 2006, which is a continuation-in-part of U.S. patent application Ser. No. 11/103,137, filed on Apr. 11, 2005, and which also claims the benefit of U.S. Provisional Application for Patent Ser. No. 60/681,863, filed May 17, 2005. The entire contents of each of these related applications is incorporated into this disclosure by reference.

TECHNICAL FIELD

The present invention relates to medical devices. More particularly, the invention relates to medical devices for implantation in a body vessel.

BACKGROUND

Various implantable medical devices are advantageously inserted within various body vessels, for example from an implantation catheter. Minimally invasive techniques and instruments for placement of intralumenal medical devices have been developed to treat and repair such undesirable conditions within body vessels, including treatment of venous valve insufficiency. Intralumenal medical devices can be deployed in a vessel at a point of treatment, the delivery device withdrawn from the vessel, and the medical device retained within the vessel to provide sustained improvement in vascular valve function. For example, implantable medical devices can function as a replacement venous valve, or restore native venous valve function by bringing incompetent valve leaflets into closer proximity. Such devices can comprise an expandable frame configured for implantation in the lumen of a body vessel, such as a vein. Venous valve devices can further comprise features that provide a valve function, such as opposable leaflets.

Implantable medical devices can comprise frames that are highly compliant, and therefore able to conform to both the shape of the lumen of a body vessel as well as respond to changes in the body vessel shape. Dynamic fluctuations in the shape of the lumen of a body vessel pose challenges to the design of implantable devices that conform to the interior shape of the body vessel. The shape of a lumen of a vein can undergo dramatic dynamic change as a result of varying blood flow velocities and volumes there through, presenting challenges for designing implantable intralumenal prosthetic devices that are compliant to the changing shape of the vein lumen.

For some applications, an implantable frame having a radial strength that varies over time upon implantation is desirable. In particular, optimizing the degree to which a medical device for implantation within a body vessel is compliant to changes in the shape of the body vessel can involve consideration of various factors. For example, a medical device comprising a highly compliant frame can minimize distortion of a body vessel by being highly responsive to changes in the shape of the body vessel.

For treatment of many conditions, it is desirable that implantable medical devices comprise remodelable material. Implanted remodelable material provides a matrix or support for the growth of new tissue thereon, and remodelable material is resorbed into the body in which the device is implanted. Common events during this remodeling process include: widespread neovascularization, proliferation of granulation mesenchymal cells, biodegradation/resorption of implanted remodelable material, and absence of immune rejection. By this process, autologous cells from the body can replace the remodelable portions of the medical device.

Mechanical loading of remodelable material during the remodeling process has been shown to advantageously influence the remodeling process. For example, the remodeling process of one type of remodelable material, extracellular matrix (ECM), is more effective when the material is subject to certain types and ranges of mechanical loading during the remodeling process. See, e.g., M. Chiquet, "Regulation of extracellular matrix gene expression by pressure," Matrix Biol. 18(5), 417-426 (October 1999). Mechanical forces on a remodelable material during the remodeling process can affect processes such as signal transduction, gene expression and contact guidance of cells. See, e.g., V C Mudera et al., "Molecular responses of human dermal fibroblasts to dual cues: contact guidance and mechanical load," Cell Motil. Cytoskeleton, 45(1):1-9 (June 2000). An earlier study by C A Tozzi et al, found that: (1) pulmonary vascular endothelial cells responded to mechanical tension by producing PDGF-like material and (2) a 4-hour application of 50 mmHg hydrostatic pressure to cultured pulmonary artery endothelial cells induced v-sis expression, suggesting that "certain vascular cells can respond to an applied load by elaborating factors that affect growth and matrix production of surrounding cells in the blood vessel wall." See C A Tozzi et al., "Pressure-induced connective tissue synthesis in pulmonary artery segments is dependent on intact endothelium," J Clin Invest. 84(3), pp. 1005-1012, 1011 (1989).

Therefore, a highly compliant frame with minimal radial strength may provide inadequate mechanical loading to material attached to the frame to allow or promote certain desirable processes to occur within the attached material, such as remodeling, or within the body vessel. In some instances, frame radial strength can be a trade-off between enabling the remodeling of material attached to the frame, and minimizing the distortion or disruption of the body vessel. Implantable endolumenal stent frames comprising a tubular, radially compressible and axially flexible structure having one or more controlled fracture initiation sites have been disclosed, for example, in published U.S. patent application Ser. No. 10/742,943 by Stinson, published as US2004/0138738 A1. However, there still exists a need in the art for an implantable prosthetic device frame that is capable of balancing concerns of conforming to the shape of a body vessel lumen and providing optimal tension on a remodelable material attached to the frame.

What is needed are medical devices that provide a radial strength that changes over time so as to provide a reduced amount of tension on a remodelable material after implantation within a body vessel for a desired period of time.

SUMMARY

Implantable frames with radial strength that can vary with time under certain conditions are adapted to provide desired levels of radial strength upon implantation within a body vessel. Medical devices with variable radial strength can provide, for example, an optimal amount of tension on an attached remodelable material during the remodeling process, and then provide increased radial strength and minimal body vessel distortion after the remodeling process is completed.

Endolumenal medical devices are provided that comprise a support frame and a remodelable material maintained under tension in a first direction by the support frame. The support frame preferably includes a means for reducing the tension on the remodelable material in the first direction, such as a weakened frame portion. Preferably, the remodelable material is tensionably attached to the support frame to maintain the remodelable material under tension in a first direction. The weakened frame portion is preferably adapted to reduce the tension on the remodelable material after a desired period of implantation within a body vessel. For example, the tension on the remodelable material can decrease when the weakened frame portion fractures or weakens after a period of time effective for the formation of remodeled tissue in place of the remodelable material. The endolumenal medical device can have any suitable configuration and function, including valves, stents, grafts, stent grafts, and shunts.

For example, an endolumenal medical device may comprise a support frame including a frame member having a weakened frame portion and a valve leaflet comprising a remodelable material tensionably attached between the two struts of the frame member; the remodelable material having a first tension in a first direction, wherein fracturing of the weakened frame portion or a decrease in the cross sectional area of the weakened frame portion of the arcuate member decreases the tension of the remodelable material in the first direction.

The endolumenal medical device is preferably configured as a valve means for providing substantially unidirectional fluid flow through a body vessel. The valve means can include a valve leaflet attached to a support frame along at least one edge of the valve leaflet to a portion of the support frame comprising the weakened frame portion. Preferably, attachment of the valve leaflet to the support frame provides a tension on the valve leaflet in a first direction perpendicular to the direction of fluid flow through the valve means, and the tension can be reduced by weakening the support member. Weakening of the support member preferably occurs by the controlled fracture of the support member at the weakened frame portion or the reduction of the cross sectional area of the support member at the weakened frame portion.

Preferably, the endolumenal medical device is a percuteneously implantable valve formed by attaching a remodelable material to a radially expandable support frame having a weakened frame portion. The remodelable material can form a valve leaflet attached to the support frame with a first tension in a first direction; wherein weakening of the support member by the controlled fracture of the support member at the weakened frame portion or the reduction of the cross sectional area of the support member at the weakened frame portion results in a decrease in the tension of the remodelable material in the first direction. The remodelable material is preferably attached to the support member at two or more attachment points. A controlled fracture initiation site can be positioned between at least two of the attachment points. The support member can define the perimeter of an opening in the support frame having three or more sides and the attachment points are positioned along the perimeter, and the opening in the support frame is preferably covered by the remodelable material maintained under tension by attachment to the support frame. The valve leaflet is preferably attached to a support member on at least two sides, and positioned within the tubular lumen of the support frame. The support frame can be configured as a tubular, radially compressible structure having a lumenal surface defining a tubular lumen and comprising a plurality of support members defining the tubular lumen the support frame. The remodelable material can be configured as a tube attached to the support frame to form a stent graft or other fluid conduit.

In a first embodiment, the weakened frame portion is a controlled fracture initiation site. Weakening of the support member by the controlled fracture of the support member at the weakened frame portion preferably results in a decrease in the tension of the remodelable material. The controlled fracture initiation site can include any suitable material adapted to fracture in a controlled manner after exposure to physiological conditions, such as conditions within a body vessel, for example in response to any suitable condition that could be present in a body vessel, such as physical conditions (e.g., physical deformation, temperature, pH, dissolution, fluid pressure, and the like) or biochemical processes (e.g., enzyme digestion, chemical reactions, and the like). The controlled fracture initiation site may also be designed to fracture after a desirable period of time, such as the time for a process occurring during tissue remodeling. For example, a frame may fracture after substantial growth of endothelial cells around or into the frame. Preferably, the medical device is designed to protect the body vessel from damage during or after the fracture of the frame material.

In a second embodiment, a medical device can comprise one or more bioabsorbable materials. Upon implantation, absorption of the bioabsorbable material within the body can reduce the cross sectional area of the support frame at the weakened frame portion, thereby increasing the flexibility of the support frame at the weakened frame portion. Weakening of the support member by the reduction of the cross sectional area of the support member at the weakened frame portion preferably results in a decrease in the tension of the remodelable material in the first direction. In one aspect, absorption of a biomaterial can decrease the radial strength of an implanted frame, for example by reducing the cross section or surface area of a portion of the frame. In another aspect, absorption of the bioabsorbable material can allow for the controlled fracture of a portion of the frame, resulting in a sudden change in the radial strength of the frame. The frame itself, or any portion of the frame, can be made from a bioabsorbable material.

The implantable medical devices can be used, for example, in methods of treating a subject, which can be animal or human, comprising the step of implanting one or more medical devices as described herein. In some embodiments, methods of treating may also include the step of delivering a medical device to a point of treatment in a body vessel, or deploying a medical device at the point of treatment. Some methods further comprise the step of implanting one or more medical devices each comprising a frame attached to one or more valve leaflets, as described herein. Methods for treating certain conditions are also provided, such as venous valve insufficiency, varicose veins, esophageal reflux, restenosis or atherosclerosis.

Methods for delivering a medical device to any suitable body vessel are also provided, such as a vein, artery, biliary duct, ureteral vessel, body passage or portion of the alimentary canal. In some embodiments, medical devices having a frame with a compressed delivery configuration with a very low profile, small collapsed diameter and great flexibility, may be able to navigate small or tortuous paths through a variety of body vessels. A low-profile medical device may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may or may not require a sheath covering the medical device. Some embodiments provide methods of making or using medical devices as described herein.

BRIEF DESCRIPTION OF THE DRAWINGS

FIG. 1B is a side view of the tubular configuration of the implantable frame shown in FIG. 1A.

DETAILED DESCRIPTION

Figure 1A:
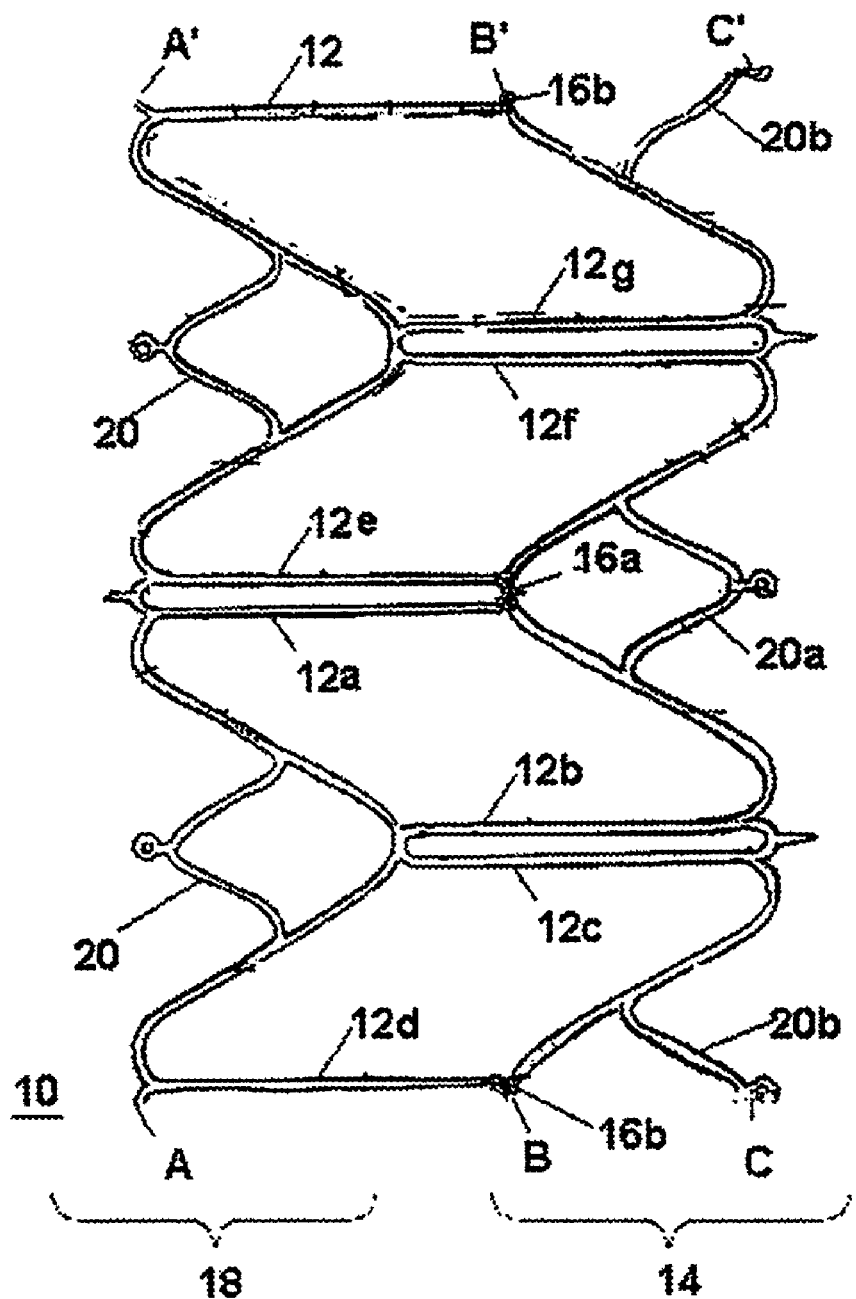
FIG. 1A is a schematic flat plan view of an implantable frame.

The following detailed description and appended drawings describe and illustrate various exemplary embodiments. Various medical devices for implantation in a body vessel, methods of making the medical devices, and methods of treatment that utilize the medical devices are provided herein.

The invention provides medical devices for implantation in a body vessel, methods of making the medical devices, and methods of treatment that utilize the medical devices.

As used herein the terms "comprise(s)," "include(s)," "having," "has," "contain(s)," and variants thereof, are intended to be open-ended transitional phrases, terms, or words that do not preclude the possibility of additional acts or structure.

The term "effective amount" refers to an amount of an active ingredient sufficient to achieve a desired affect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the composition of the present invention.

As used herein, the term "body vessel" means any body passage cavity that conducts fluid, including but not limited to biliary ducts, pancreatic ducts, ureteral passages, esophagus, and blood vessels such as those of the human vasculature system.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

As used herein, "endolumenally," "intralumenal" or "translumenal" all refer synonymously to implantation placement by procedures wherein the medical device is advanced within and through the lumen of a body vessel from a remote location to a target site within the body vessel. As used herein, "endolumenally" means placement by procedures wherein the prosthesis is translumenally advanced through the lumen of a body vessel from a remote location to a target site within the body vessel. In vascular procedures, a medical device will typically be introduced "endovascularly" using a catheter over a guidewire under fluoroscopic guidance. The catheters and guidewires may be introduced through conventional access sites to the vascular system, such as through the femoral artery, or brachial and subclavian arteries, for access to the coronary arteries.

The medical devices described herein are preferably radially expandable. By "radially expandable," it is meant that the body segment can be converted from a small diameter configuration (used for endolumenal placement) to a radially expanded, usually cylindrical, configuration which is achieved when the medical device is implanted at the desired target site. A medical device can be radially expanded by any suitable mechanism.

The term "biodegradable" is used herein to refer to materials selected to dissipate upon implantation within a body, independent of which mechanisms by which dissipation can occur, such as dissolution, degradation, absorption and excretion. The actual choice of which type of materials to use may readily be made by one ordinarily skilled in the art. Such materials are often referred to by different terms in the art, including "bioresorbable," "bioabsorbable," or "biodegradable," depending upon the mechanism by which the material dissipates. For the purposes of this application, unless otherwise specified, the term "biodegradable" includes materials that are "bioresorbable," and "bioabsorbable." The prefix "bio" indicates that the erosion occurs under physiological conditions, as opposed to other erosion processes, caused by, for example, high temperature, strong acids or bases, UV light or weather conditions. As used herein, "biodegradable material" includes materials, such as a polymer or copolymer, that are absorbed by the body, as well as materials that degrade and dissipate without absorption into the body. As used herein, "biodegradable polymer" refers to a polymer or copolymer which dissipates upon implantation within the body. A large number of different types of materials are known in the art which may be inserted within the body and later dissipate.

"Non-bioabsorbable" material refers to a material, such as a polymer or copolymer, which remains in the body without substantial bioabsorption.

The recitation of a "first" direction is provided as an example. Any suitable orientation or direction may correspond to a "first" direction. The medical devices of the embodiments described herein may be oriented in any suitable absolute orientation with respect to a body vessel. For example, the first direction can be a radial direction in some embodiments.

"Radial strength" (also called "hoop strength") refers to the ability of a medical device to resist external circumferential pressure directed radially inward toward the center of a cross sectional area of the medical device, as measured by the change in diameter of the medical device as a function of inward circumferential pressure. A reduction in radial strength over time is measured by comparing the frame displacement in response to a force applied to the frame in the same manner at two different points in time. Preferably, the radial strength is measured using a Radial Force Gauge.

"Radial expansion force" refers to the outward radial force exerted by the expansion of a medical device from a radially compressed configuration.

Preferably, the medical device comprises a frame having a first radial strength in an inward radial direction, and a material or structure to decrease the radial strength of the frame along the inward radial direction after implantation of the frame in a body vessel. Also preferably, a decrease in radial strength occurs in response to conditions within a body vessel. The decrease in radial strength of the frame upon implantation can occur in several ways. For example, a portion of a frame can be bioabsorbed or fracture in a controlled fraction to reduce the radial strength of the frame. In some embodiments, the frame can comprise various materials or configurations to provide a reduced radial strength after a period of time after implantation.

Preferably, the medical devices described herein comprise an endolumenally-implantable frame having a first radial strength and a means for reducing the radial strength within a body vessel. Preferably, the frame is designed to undergo a reduction in radial strength in response to conditions typically encountered in a body vessel in which the frame is intended to be implanted. More preferably, the frame is designed to undergo a reduction after a desirable period of exposure to such conditions.

Medical Devices Comprising an Implantable Frame

In a first embodiment the medical device frame comprises a material that is mechanically altered to reduce the radial strength of the frame after exposure to one or more physiological conditions, such as conditions within a body vessel, for a desirable period of time. Mechanical alteration of the frame can include increased flexibility of the frame, or portions thereof, cracking or breaking of portions of the frame. The mechanical alteration of the frame can result from any suitable condition, including physical or biochemical characteristics found within a body vessel.

In one aspect, the frame, or portions thereof, is designed to bend, crack or break upon exposure of the frame to conditions present in a body vessel for a desirable period of time. For example, a frame can be designed to reduce its radial strength in response to physical conditions within a body vessel. Physical conditions in a body vessel include physical deformation or movement, body temperature, fluid pH, degree of solubility of the frame in fluid found in a body vessel, fluid pressure, and the like. A frame can also be designed to reduce its radial strength in response to biochemical conditions or processes within a body vessel. Biochemical processes include enzyme digestion, chemical reactions, and the like.

A frame may comprise one or more weakened frame portions designed to undergo mechanical alteration in response to conditions encountered in a body vessel. In one aspect, a frame comprises one or more weakened frame portions positioned along the frame such that mechanical alteration of the weakened frame portion reduces the overall radial strength of the frame. A "weakened frame portion" or "weakened frame portion" refer synonymously to the relative stiffness or resistance of a weakened region to mechanical alteration such as bending, cracking or breaking, compared to the susceptibility of any adjacent region of the frame to such mechanical alteration. In one aspect, the weakened frame portions are bent frame regions that are more flexible than adjacent frame regions. In another aspect, the weakened frame portions are more likely to fracture (i.e., crack or break) after a desired period of exposure to one or more physiological conditions in a body vessel.

In one aspect, an implantable frame is a serpentine or zig-zag structure comprising a plurality of parallel, adjacent struts, some of which are joined by weakened frame portions between pairs of struts. Referring to FIG. 1A, a flat plan view of an implantable frame 10 includes a first hoop 14 connected to a second hoop 18 by a plurality of struts 12, including struts labeled 12a, 12b, 12c, 12d, 12e, 12f and 12g. The implantable frame can be assembled from a flat plan view in FIG. 1A to a cylindrical configuration shown in FIG. 1B by "rolling" the frame to join points A to A', B to B' and C to C'. FIG. 1B shows a side view of the frame in FIG. 1A in the radially-expanded, cylindrical configuration. The cylindrical configuration is radially symmetric about a longitudinal axis 2 passing through the lumen of the frame 10. Preferably, the frame 10 is formed in the cylindrical configuration by laser-cutting the array of hoops 14, 18 and struts 12 from a cylinder of self-expanding material. The frame 10 may further include a plurality of reinforcing members 20, including reinforcing members 20a and 20b. The frame 10 in the cylindrical configuration may be radially compressed around the longitudinal axis 2 by crimping the frame around a catheter delivery device, and then radially expanded at a site of implantation within a body vessel to the radially expanded configuration of FIG. 1B.

The frame 10 may further include weakened frame portions 16a and 16b, which are configured to reduce the radial expansion force of the frame 10 when weakened or broken. The frame 10 is preferably formed from a self-expanding material that permits the frame 10 to exert a force directed radially outward from the longitudinal axis 2 when the frame 10 is less than fully radially expanded (i.e., when the frame 10 has a radius that is less than the fully-expanded radius shown in FIG. 1B). The outward radial force of the frame 10 is reduced when the weakened frame portions 16a and/or 16b are weakened or broken.

The relative weakness and strength of the various weakened frame portions, such as weakened frame portion 16a, can be obtained in a variety of ways. For example, it may be possible to selectively treat individual frame regions with heat, radiation, mechanical working, or combinations thereof, so that the mechanical characteristics of the hinge region are altered, i.e., so that selected hinge regions will bend, crack or break with a greater or lesser force than others of the hinge regions.

In one aspect, the strength of the weakened frame portions can be controlled by selecting the relative cross-sectional dimensions of the different frame regions. Usually, the weakened frame portions will have cross-sectional dimensions which are selected so that the force required to bend, crack or sever the weakened frame portion is less than that required for other non-weakened frame portions. Usually, the weakened frame portion will have a section in which the height in the radial direction remains constant (i.e. it will be the same as the remainder of the frame) while the width in the circumferential direction will be reduced about 20-30% relative to the non-weakened hinge regions. The terms "weakened" and "non-weakened" are relative terms, and it would be possible to augment or increase the width of the non-weakened regions relative to the weakened regions. It will also be possible to provide two or more discrete narrowings within a single weakened frame portion, or to provide one or more narrowings in the regions of the struts immediately adjacent to the weakened frame portions. In another aspect, a weakened frame portion may be created by cutting notches or voids into a portion of the frame. For example, V-shaped notches may be cut into the hinge region on the side which undergoes compression during opening of the hinge. Alternatively, the frame can be sanded or beveled to create a weakened frame portion.

Figure 2A:
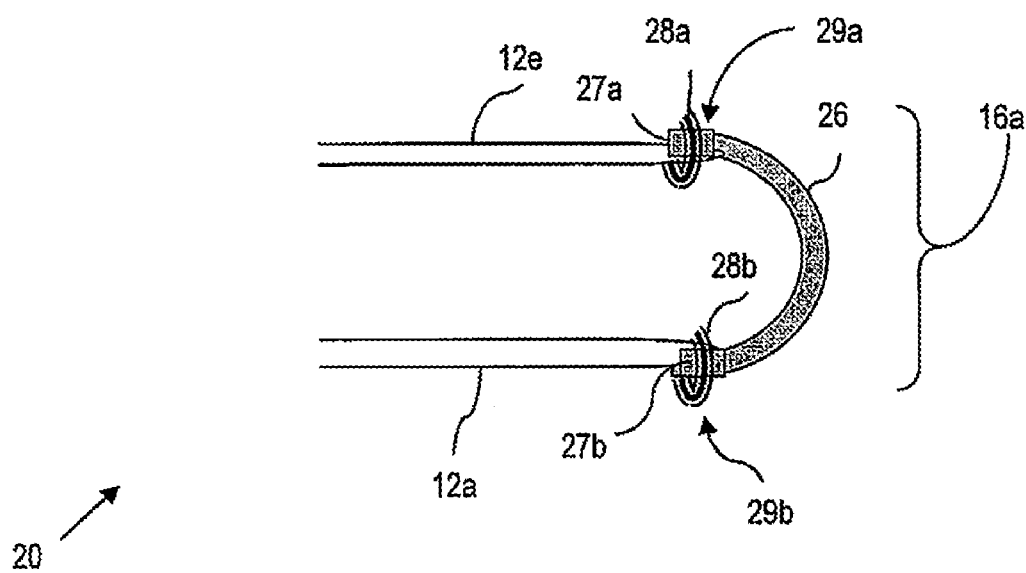
FIG. 2A is a detail view of a weakened frame portion of an implantable frame comprising a fracture initiation site.

In yet another aspect, a weakened frame portion can be created altering one or more joints between portions of a frame in response to one or more conditions in a body vessel. For example, the frame can comprise separate segments that are joined together with an adhesive that is gradually dissolved in fluid within a body vessel, such as blood. For example, the frame 10 in FIG. 1A or FIG. 1B can comprise weakened frame portion 16a, as depicted in frame portion 20 of FIG. 2A. Referring to FIG. 2A, a frame portion 20 comprises a weakened frame portion 16a including two substantially parallel struts, 12a, 12e, joined to a curved "elbow" frame segment 26. The weakened frame portion 16a further comprises a first dislocating joint 29a and a second dislocating joint 29b between a first strut 12a and a second strut 12e each attached to opposite ends of a curved "elbow" frame segment 26 in the middle. Upon implantation in a body vessel, weakened frame portion 16a has a first configuration 20. When the frame is in the first configuration 20, a first biodegradable adhesive 27a joins the first strut 12a to the curved elbow frame segment 26 at the first dislocating joint 29a, and a second biodegradable adhesive 27b joins the second strut 12e to the opposite end of the elbow frame segment 26 at the second dislocating joint 29b. The curved elbow frame segment 26 forms a bent structure, and can be made from any material with an appropriate level of flexibility. For example, one or more struts or elbow frame segments 26 can comprise a bioabsorbable material or a non-bioabsorbable material, a remodelable material, or any combination thereof. An elbow frame segment 26 can also be designed to partially fracture in response to force above a desired threshold level. A plurality of flexible retaining rings 28a, 28b encircle the joints of the first strut 12a and the second strut 12e to the elbow frame segment 26. The weakened frame portion 16a has a first radial strength in the first configuration 20.

Figure 2B:
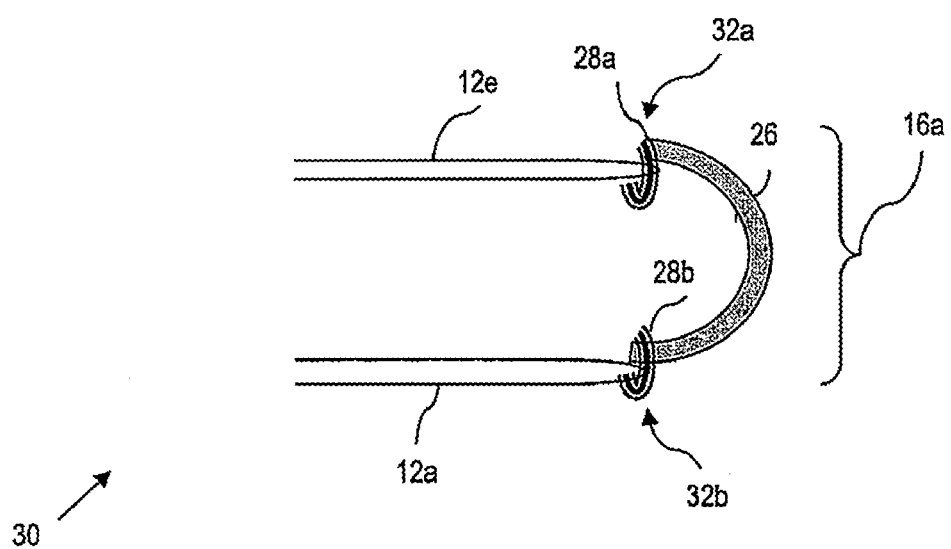
FIG. 2B is a detail view of the portion of an implantable frame shown in FIG. 2A, after a controlled fracture of the frame portion.

After implantation in a body vessel for a desired period of time, the first biodegradable adhesive 27a and the second biodegradable adhesive 27b are dissolved, resulting in a decrease in the radial strength of the frame in a second configuration 30, including weakened frame portion 16a as depicted in FIG. 2B. In FIG. 2B, a portion of the weakened frame portion 16a is shown in the second configuration 30, with a second radial strength that is less than the first radial strength of the frame when weakened frame portion 16a in the first configuration 20. In the second configuration 30, the first flexible retaining ring 28a permits the first strut 12a to move relative to the elbow frame segment 26 within a first gap region 32a. Similarly, a second flexible retaining ring 28b permits the second strut 12e to move relative to the elbow frame segment 26 within a second gap region 32b. Movement of the frame components within a plurality of gap regions 32a, 32b reduces the radial strength of the frame by allowing the struts to move in a confined manner with respect to the adjacent elbow frame segments. Overall, the frame comprises a plurality of interconnected struts and elbow frame segments arranged around a cylindrical form. Preferably, the medical device is designed to protect the body vessel from damage during or after the fracture of the frame material. In one aspect, the frame is designed to undergo a controlled fracture, meaning that the fracture does not harm surrounding tissue. In one aspect, a flexible sleeve comprising an elastic polymeric material can be wrapped around weakened regions in the frame. For example, in FIG. 2B, the first flexible retaining ring 28a and the second flexible retaining ring 28b prevent an end of the first strut 12a or an end of the second strut 12e, respectively, from extending into surrounding tissue within the body vessel.

The frame can further comprise any suitable structure to protect surrounding tissue from undesirably contacting the body vessel wall. In one aspect, the frame can fracture without presenting exposed sharpened ends to surrounding tissue. In another embodiment, the frame can cleanly break, and the fractured ends of the frame can be shielded from the surrounding material, for example by an elastic retaining sleeve. In another embodiment, the frame can be embedded in remodeled tissue when the fracture occurs, and the frame can be designed to fracture in a manner that will not harm surrounding tissue (for example, by crumbling and then being bioabsorbed). Preferably, the frame is designed to comply with applicable governmental regulatory guidelines promulgated, for example, by the FDA. In one aspect, the adjacent portions of the frame are tethered together so that when the adhesive dissolves, the adjacent segments of the frame remain closely associated but slightly moveable with respect to each other. Relative movement of the adjacent frame segments preferably reduces the radial strength of the overall frame.

In a second embodiment, the medical device frame comprises a material that is chemically altered or absorbed to reduce the radial strength of the frame after exposure to one or more physiological conditions for a desirable period of time. According to this embodiment, the medical device preferably comprises one or more bioabsorbable materials. The frame itself, or any portion of the frame, can be made from a bioabsorbable material. In one aspect, a weakened frame portion can comprise a bioabsorbable material.

In one aspect, absorption of a biomaterial can decrease the radial strength of an implanted frame, for example by reducing the cross section or surface area of a portion of the frame. In some aspects, absorption of a portion of the frame comprising bioabsorbable material can allow for the controlled fracture of a portion of the frame, resulting in a sudden change in the radial strength of the frame.

Methods of engineering planned implantable frame disintegration and/or fracture may include but are not limited to: controlling the formation of heterogeneous structure of amorphous and crystalline regions within the stent or stent filaments, creating multiple internal or surface fracture initiation sites, creating localized predegraded material, or using multiple strands with small section size to construct the stent.

One method of creating multiple fracture initiation sites in a biodegradable polymer is to create periodic regions of pre-degraded material along a stent or a structural element of a stent, such as a monofilament. Post-extrusion or molding operations such as localized degradation of molecular weight of crystalline materials may be performed with lasers, focal UV light sources, water or steam hydrolysis, or irradiation. When the material is presented into an environment that provides heat and moisture for hydrolytic polymer degradation, the pre-degraded regions will lose strength and disintegrate sooner than regions of the material that were not pre-degraded. The frequency of occurrence of the pre-degraded regions will affect the size of the fracture pieces from disintegration. A low frequency of predegradation regions will result in disintegration into relatively large pieces. A high frequency will result in disintegration into relatively small pieces.

In addition to, or as an alternative to, manipulating the molecular structure of polymer support frame materials, mechanical disintegration and/or fracture sites may be designed into the implant to cause predictable, controlled fracture and/or disintegration. Mechanical disintegration initiation sites may be created in the material or implant, for example, by purposely notching, grooving, indenting, or contouring the surface. Internal mechanical initiation sites may be created by purposely introducing porosity or foreign particles in the solidifying polymer.

Preferably, the exposure of the bioabsorbable material under one or more conditions present in a body vessel results in the reduction of the radial strength of the frame. In one aspect, bioabsorbable materials are disposed within the frame so that absorption of the bioabsorbable material results in a desired amount and manner of radial strength reduction. In one aspect, increased flexibility is imparted to a weakened frame portion by incorporating a bioabsorbable material into the weakened frame portion of the frame. In another aspect, a portion of a frame comprising a bioabsorbable material easily breaks after absorption of all or part of the bioabsorbable material.

In some embodiments, the radial strength of the frame can be designed to decrease after a period of time following implantation, and the radial strength can change suddenly or gradually. The change in radial strength of the frame can occur by various mechanisms. For example, the radial strength of a frame comprising a bioabsorbable material can gradually decrease with the bioabsorption of the bioabsorbable material after implantation. In another embodiment, the bioabsorption of a bioabsorbable support arm can result in a fracture of the arm in response to shear forces of blood flow, thereby suddenly decreasing the radial strength of the frame. In another embodiment, micro fractures in portions of the frame can increase the flexibility of portions of the frame, thereby decreasing the radial strength of the frame along a first direction.

Diminution in the radial strength of the frame can occur gradually over any desirable time period. The time period after implantation when the frame can decrease radial strength can, in some embodiments, be similar to the time period for bioabsorption of various bioabsorbable materials used to construct the frame. Other aspects provide a frame with a radial strength that decreases as a safety feature in response to a sudden pressure along a first direction so as to prevent damage to the lining of a body vessel. Still other aspects provide a frame that decreases radial strength after a pre-determined period of implantation, for example, within about 3 weeks, about 2 weeks or about 1 week. In preferred aspects, the frame can decrease radial strength after a longer period of time, such as at least 30 days, including periods of 44, 58, 72, 86, 90 100, 114, 128, 142, 156, 170, 180, or 184 days, or longer, and any number of days therebetween. Preferably, selection of the bioabsorbable materials, and the configuration of the bioabsorbable materials in the implantable frame, can be chosen to provide a desirable time period of bioabsorption of the material and the accompanying decrease in radial strength after implantation.

An implantable frame can comprise any suitable configuration of bioabsorbable material. In one embodiment, the frame can further comprise a first bioabsorbable material or a non-bioabsorbable material as a "core" material. The core material can be at least partially enclosed by a second bioabsorbable material. The frame can also comprise a surface area presenting both a bioabsorbable material and a non-bioabsorbable material, and absorption of the bioabsorbable material can increase the surface area, resulting in a decrease of the radial strength of the frame in a first direction. The frame can further include one or more support arms comprising a bioabsorbable material, and absorption of the bioabsorbable material can decrease the radial strength of the frame in a first direction.

Figure 3A:
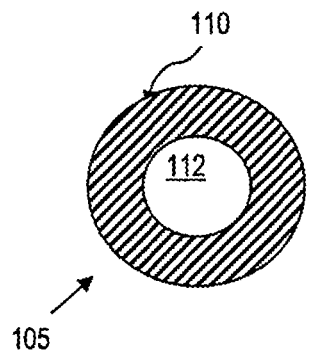
FIG. 3A is a cross sectional view of a weakened frame portion of an implantable frame comprising a bioabsorbable material disposed on the surface of a non-bioabsorbable material in a first configuration.

The frame 10 in FIG. 1A or FIG. 1B can comprise weakened frame portion 16a having a cross section as depicted in FIG. 3A. The cross section 105 of weakened frame portion 16a or 16b in FIGS. 1A-1B may be used as the weakened frame portion instead of, or in combination with, the configuration 20 shown in FIG. 2A. FIG. 3A shows a cross section 105 comprising a non-bioabsorbable core material 112 (e.g., a self-expanding metal alloy) surrounded by a bioabsorbable material 110. Bioabsorption of the bioabsorbable material 110 decreases the radial strength of the frame 10 at the weakened frame portion 16a in FIG. 1B. When implanted in a body vessel, the outer layer 110 is bioabsorbed, thereby increasing the flexibility of the frame 10 at the weakened frame portion 16a and decreasing the radial strength of the frame 10.

Figure 3B:
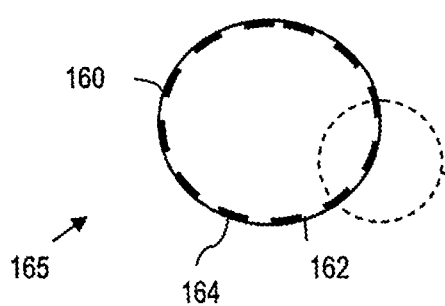
FIG. 3B is a cross sectional view of a weakened frame portion of an implantable frame comprising a bioabsorbable material disposed on the surface of a non-bioabsorbable material in a second configuration.
Figure 3C:
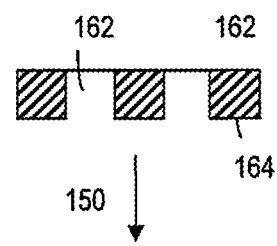
FIG. 3C is a detail view of a portion of the cross sectional view in FIG. 3B.
Figure 3C:

FIG. 3B is an alternative cross section 165 to the cross section 105 in FIG. 3A, of the weakened frame portion 16a or 16b in FIGS. 1A-1B. The cross section 165 comprises a flexible non-bioabsorbable core material 162 having a series of grooves, wells or holes 160 on the surface that are at least partially filled with a rigid bioabsorbable material 164. Bioabsorption of the bioabsorbable material 164 decreases the radial strength of the frame by permitting the non-bioabsorbable core material 162 (e.g., a flexible metal or metal alloy or a flexible rubber or polymeric material) to bend more easily in the absence of the rigid bioabsorbable material 164. FIG. 3C is a detailed close-up view of a portion of the cross section 165, showing a series of indentations (such as grooves or pits) along the surface of the flexible non-bioabsorbable material 162. Rigid bioabsorbable material 164 is deposited in the indentations. Upon implantation, the bioabsorbable material 164 is bioabsorbed 150 and the flexibility of a weakened frame portion 16a comprising the non-bioabsorbable material 162 is gradually increased.

Bioabsorbable Materials

An implantable frame can comprise any suitable bioabsorbable material, or combination of bioabsorbable materials. For example, the weakened frame portion (including regions 16a or 16b in frame 10 in FIG. 1A) can comprise a biodegradable or bioabsorbable material. For example, the weakened frame portion 16a can be formed entirely from a segment of a bioabsorbable material, the weakened frame portion 16a can have a configuration 20 shown in FIG. 2A, the weakened frame portion 16a can have a cross section configuration 105 shown in FIG. 3A or the weakened frame portion 16a can have the cross section configuration 165 shown in FIGS. 3B-3C. The types of bioabsorbable materials are preferably selected to provide a desired time scale for diminution in the radial strength of the frame. Variations in selected times for bioabsorption may depend on, for example, the overall health of the patient, variations in anticipated immune reactions of the patient to the implant, the site of implantation, and other clinical indicia. Bioabsorbable materials may be selected to form at least a portion of a frame so as to provide an decreased frame radial strength after a particular period of time. In certain embodiments, bioabsorption of a biomaterial in a frame can decrease the radial strength of the frame in a first direction. In some embodiments, the frame may be designed to bend radially inward in response to a pressure.

The bioabsorbable material may comprise any suitable composition, including without limitation, a polyester, a polyester-ethers, a copoly(ether-esters), a poly(hydroxy acid), a poly(lactide), a poly(glycolide), or co-polymers and mixtures thereof. In another aspect, the bioabsorbable material is poly(p-dioxanone), poly(epsilon-caprolactone), poly (dimethyl glycolic acid), poly(D,L-lactic acid), L-polylactic acid, or glycolic acid, poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, poly(hydroxy butyrate), polydioxanone, PEO/PLA or a co-polymer or mixture thereof. Bioabsorbable materials further include modified polysaccharides (such as cellulose, chitin, and dextran), modified proteins (such as fibrin and casein), fibrinogen, starch, collagen and hyaluronic acid. The bioabsorbable material may also be, without limitation, hydroxyethyl starch, gelatin, and derivatives of gelatin.

In one aspect, an implantable frame, or a portion thereof, comprises a bioabsorbable material selected from the following group of FDA-approved polymers: polyglycolic acid (PGA), polylactic acid (PLA), Polyglactin 910 (comprising a 9:1 ratio of glycolide per lactide unit, and known also as VICRYL™), polyglyconate (comprising a 9:1 ratio of glycolide per trimethylene carbonate unit, and known also as MAXON™), and polydioxanone (PDS). In general, these materials biodegrade in vivo in a matter of months, although some more crystalline forms can biodegrade more slowly. These materials have been used in orthopedic applications, wound healing applications, and extensively in sutures after processing into fibers.

Other useful materials for creating weakened frame portions include those disclosed in U.S. Pat. No. 4,838,267, for example, including block copolymers derived from p-dioxanone and glycolide that exhibit a high order of initial strength but lose their strength rapidly after implantation in the body. U.S. Pat. No. 4,605,730 and U.S. Pat. No. 4,700,704 disclose copolymers of epsilon-caprolactone and glycolide that are also useful in making bioabsorbable frame portions. In addition, U.S. Pat. No. 4,624,256 discloses high molecular weight caprolactone polymers, while U.S. Pat. No. 4,429,080 discloses triblock copolymers prepared from copolymerizing glycolide with trimethylene carbonate. Homopolymers and copolymers such as those disclosed in U.S. Pat. No. 5,412,068 are also appropriate for the resorbable frame portions.

Still other bioabsorbable materials can be synthesized from protein-based polymers, particularly polymers containing elastomeric polypeptide sequences (Wong, et al., "Synthesis and properties of bioabsorbable polymers used as synthetic matrices for tissue engineering" in Synthetic Bioabsorbable Polymer Scaffolds (Atala & Mooney, eds.) pp. 51-82 (Birkhauser, Boston, 1997). Cells can invade matrices derived from these materials. U.S. Pat. Nos. 5,468,253 and 5,713,920, both to Bezwada et al., disclose other bioabsorbable elastomeric materials which are used to form devices that, based on in vitro data, are alleged to completely bioabsorb within one year or six months.

Preparation of these and other bioabsorbable polymers or copolymers are known in the art. Such polymers may be manufactured and configured as disclosed, for example, in U.S. Pat. No. 5,133,755, incorporated by reference herein. U.S. Pat. Nos. 5,705,181 and 5,393,594, relate to the preparation and use poly(lactide), poly(glycolide), poly(epsilon-caprolactone), poly(p-dioxanone), poly(epsilon-caprolactone-co-p-dioxanone) and poly(lactide-co-glycolide). U.S. Pat. No. 5,522,841, incorporated herein by reference, relates to the preparation and use of bioabsorbable block copolymers made of hard phase forming monomers, e.g., glycolide and lactide, and soft phase monomers, e.g., 1,4 dioxane-2-one and caprolactone, as described. Bioabsorbable polymers derived in whole or in part from dioxanone can be used in some embodiments. Homopolymers of p-dioxanone are described, e.g., in U.S. Pat. Nos. 3,063,967; 3,063,968; 3,391,126; 3,645,941; 4,052,988; 4,440,789; and, 4,591,630. Copolymers containing units derived from p-dioxanone and one or more other monomers that are copolymerizable therewith are described, e.g., in U.S. Pat. Nos. 4,243,775; 4,300,565; 4,559,945; 4,591,630; 4,643,191; 4,549,921; 4,653,497; 4,791,929; 4,838,267; 5,007,923; 5,047,048; 4,076,807; 5,080,665; and 5,100,433 and European Patent Application Nos. 501,844 and 460,428.

Further relevant references can include, for example, D. K. Gilding et al., "Biodegradable polymers for use in surgery-polyglycolic/poly(lactic acid) homo- and copolymers: 1," Polymer, 20: 1459-1464 (1979), and D. F. Williams (ed.), Biocompatibility of Clinical Implant Materials, Volume II, chapter 9: "Biodegradable Polymers" (1981), which are incorporated herein by reference. Polymers, copolymers and devices made from .epsilon.-caprolactone and/or related compounds have also been described in U.S. Pat. Nos. 3,169,945, 3,912,692, 3,942,532, 4,605,730, 4,624,256, 4,643,734, 4,700,704, 4,788,979, 4,791,929, 4,994,074, 5,076,807, 5,080,665, 5,085,629 and 5,100,433.

Implantable Frames

Suitable support frames can have a variety of configurations, including braided strands, helically wound strands, ring members, consecutively attached ring members, tube members, and frames cut from solid tubes. The configuration of the support frame is not limited to the frame 10 shown in FIGS. 1A-1B. Other suitable frames can have a variety of sizes. The exact configuration and size chosen will depend on several factors, including the desired delivery technique, the nature of the vessel in which the device will be implanted, and the size of the vessel. A frame structure and configuration can be chosen to facilitate maintenance of the device in the vessel following implantation.

The frame can, in one embodiment, comprise a plurality of struts. Struts are structures that can resist compression along the longitudinal axis of the strut. Struts can be an identifiable segment of an elongated frame member, for example separated by bends in the member, individual segments joined together, or any combination thereof. Struts can have any suitable structure or orientation to allow the frame to provide desirable radial strength properties to the frame. For example, struts can be oriented substantially parallel to, substantially perpendicular to, or diagonal to the longitudinal axis of a tubular frame, or some combination thereof. Struts can be straight or arcuate in shape, and can be joined by any suitable method, or can form one or more distinct rings.

In one aspect, implantable frames comprise a serpentine (or zig-zag) plurality of struts having substantially equal lengths joined together in a reversing pattern. In another aspect, implantable frames comprise repeating S-shaped hinge regions or repeating Z-shaped hinge regions. The latter pattern is commonly referred to a zig-zag stent.

In another embodiment, the frame comprises a combination of bioabsorbable and nonabsorbable polymers. Examples of synthetic biocompatible non-bioabsorbable polymers include, but are not limited to, homopolymers and copolymers of polypropylene, polyamides, polyvinylchlorides, polysulfones, polyurethanes, polytetrafluoroethylene, ethylene vinyl acetate (EVAC), polybutylmethacrylate (PBMA) or methylmethacrylate (MMA). The frame can comprise the non-absorbable polymer in amounts from about 0.5 to about 99% of the final composition. The addition of EVAC, PBMA or methylmethacrylate increases malleability of the matrix so that the device is more plastically deformable.

Various constructs of the elongate elements, fibers and threads can be formed utilizing well known techniques, e.g., braiding, plying, knitting, weaving, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. See, e.g., Mohamed, American Scientist, 78: 530-541 (1990). Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of uncrosslinked collagen and two threads of crosslinked collagen.

The dimensions of the implantable frame will depend on its intended use. Typically, the implantable frame will have a length in the range from 0.5 cm to 10 cm, usually being from about 1 cm to 5 cm, for vascular applications. The small (radially collapsed) diameter of a cylindrical frame will usually be in the range from about 1 mm to 10 mm, more usually being in the range from 1.5 mm to 6 mm for vascular applications. The expanded diameter will usually be in the range from about 2 mm to 30 mm, preferably being in the range from about 2.5 mm to 15 mm for vascular applications. The body segments may be formed from conventional malleable materials used for body lumen stents and grafts, typically being formed from metals.

Medical Devices Comprising a Remodelable Material

In a third embodiment, a medical device can comprise a frame and a remodelable material attached to the frame. Preferably, the remodelable material is subject to a mechanical load adequate to allow remodeling of the remodelable material when the frame has the first radial strength. A "mechanical load" means any force applied to a material that results in tension within the material. In preferred embodiments, a remodelable material is subject to adequate mechanical load to allow remodeling processes to occur. The phrase "tensionably attach a material to a frame" refers to attachment of a material to a frame results in a tension within the attached material. A tensionably attached material is subject to one form of a mechanical load. The tension in the material is preferably provided by the restraint of radial expansion of the frame by the material. For example, the frame may be configured as a radially self-expanding frame, and the material may be configured and attached to the frame so as to restrict the expansion of the frame. Accordingly, in one aspect, the tension in the material may be related to the degree to which the material restricts the radial expansion of a self-expanding frame. Typically, the material is tensionably attached to struts of a self-expanding frame that are positioned along the perimeter of a lumen defined by the frame, thereby restricting the radial expansion of the frame. Preferably, a remodelable material extends across the lumen defined by a radially self-expanding frame between at least two struts, thereby restricting the diameter of the frame lumen would have if fully expanded in the absence of the remodelable material.

Mechanical loading of remodelable material during the remodeling process can advantageously influence the remodeling process. For example, the remodeling process of one type of remodelable material, extracellular matrix (ECM), is more effective when the material is subject to certain types and ranges of mechanical loading during the remodeling process. See, e.g., M. Chiquet, "Regulation of extracellular matrix gene expression by pressure," Matrix Biol. 18(5), 417-426 (October 1999). Applying mechanical forces to a remodelable material during the remodeling process is believed to affect processes such as signal transduction, gene expression and contact guidance of cells. Various references describe the influence of mechanical loading on remodelable materials, such as extracellular matrix material (ECM). For example, mediation of numerous physiological and pathological processes by vascular endothelial cells is influenced by mechanical stress, as discussed, for example, in Chien, Shu et al., "Effects of Mechanical Forces on Signal Transduction and Gene Expression in Endothelial Cells," Hypertension 31(2): 162-169 (1998). Expression of bioactive agents can be stimulated by mechanical stress on certain cells involved in remodeling processes, such as fibroblasts, as discussed, for example, by Schild, Christof et al., "Mechanical Stress is Required for High-Level Expression of Connective Tissue Growth Factor," Experimental Cell Research, 274: 83-91 (2002). Furthermore, another study suggests that fibroblasts attached to a remodelable material such as a strained collagen matrix produce increased amounts of ECM glycoproteins like tenascin and collagen XII compared to cells in a relaxed matrix. Chiquet, Matthias, et al., "Regulation of Extracellular Matrix Synthesis by Mechanical Stress," Biochem. Cell. Biol., 74:737-744 (1996). Other studies of remodelable material have found that remodeling processes are sensitive to alterations in mechanical load. See, e.g., Wong, Mary et al., "Cyclic Compression of Articular Cartilage Explants is Associated with Progressive Consolidation and Altered Expression Pattern of Extracellular Matrix Proteins," Matrix Biology, 18: 391-399 (1999); Grodzinsky, Alan J. et al., "Cartilage Tissue Remodeling in Response to Mechanical Forces," Annual Review of Biomedical Engineering, 2: 691-713 (2000). In addition, the alignment of cells with respect to mechanical loads can affect remodeling processes, as studied, for example, by V C Mudera et al., "Molecular responses of human dermal fibroblasts to dual cues: contact guidance and mechanical load," Cell Motil. Cytoskeleton, 45(1):1-9 (June 2000). These references are incorporated herein by reference.

To facilitate ingrowth of host or other cells during the remodeling process, either before or after implantation, a variety of biological response modifiers may be incorporated into the remodelable material. Appropriate biological response modifiers may include, for example, cell adhesion molecules, cytokines, including growth factors, and differentiation factors. Mammalian cells, including those cell types useful or necessary for populating the resorbable stent of the present invention, are anchorage-dependent. That is, such cells require a substrate on which to migrate, proliferate and differentiate.

In some embodiments, upon implantation in a body vessel, a remodelable material can be subject to both a mechanical load, for example from the manner of attachment to a frame, as well as a variable shear stress from the fluid flow within the body vessel. For example, Helmlinger, G. et al., disclose a model for laminar flow over vascular endothelial cells in "Calcium responses of endothelial cell monolayers subjected to pulsatile and steady laminar flow differ," Am. J. Physiol. Cell Physiol. 269:C367-C375 (1995). Shear forces within a body vessel can also influence biological processes involved in remodeling. For example, the role of hemodynamic forces in gene expression in vascular endothelial cells is discussed by Li, Y. S. et al., "The Ras-JNK pathway is involved in shear-induced gene expression," Mol. Cell Biol., 16(11): 5947-54 (1996). Many other studies of the range of shear forces and the effect of shear forces on the remodeling process are found in the art. Using these references and others, one skilled in the art can select a level of mechanical loading that, when taking into account the range of fluid flow shear forces within a body vessel, will provide optimal mechanical loading conditions for remodeling of the remodelable material.

Reconstituted or naturally-derived collagenous materials can be used as remodelable materials. Such materials that are at least bioresorbable will provide advantage in the present invention, with materials that are bioremodelable and promote cellular invasion and ingrowth providing particular advantage. Suitable bioremodelable materials can be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or mufti-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 .mu·g/mg, more preferably less than about 2 .mu·g/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Medical Devices Comprising a Means for Regulating Fluid Flow

In a fourth embodiment, the medical device can comprise a means for regulating fluid through a body vessel. In some embodiments, the fluid can flow through an implantable frame, while other embodiments provide for fluid flow through a lumen defined by the frame. In some aspects, a frame and a first valve leaflet are connected to a frame.

A valve leaflet, according to some aspects, can comprise a valve leaflet, such as a leaflet comprising a free edge, responsive to the flow of fluid through the body vessel. A "free edge" refers to a portion of a leaflet that is not attached to a frame, but forms a portion of a valve orifice. Preferably a leaflet free edge is a portion of the edge of the leaflet that is free to move in response to the direction of fluid flow in contact with the leaflet, independently of the movement of the frame.

Preferably, one or more valve leaflets attached to a frame may, in one embodiment, permit fluid to flow through a body vessel in a first direction while substantially preventing fluid flow in the opposite direction. In some embodiments, the valve leaflet comprises an extracellular matrix material, such as small intestine submucosa (SIS). The valve leaflet can be made from any suitable material, including a remodelable material or a synthetic polymer material.

Figure 4A:
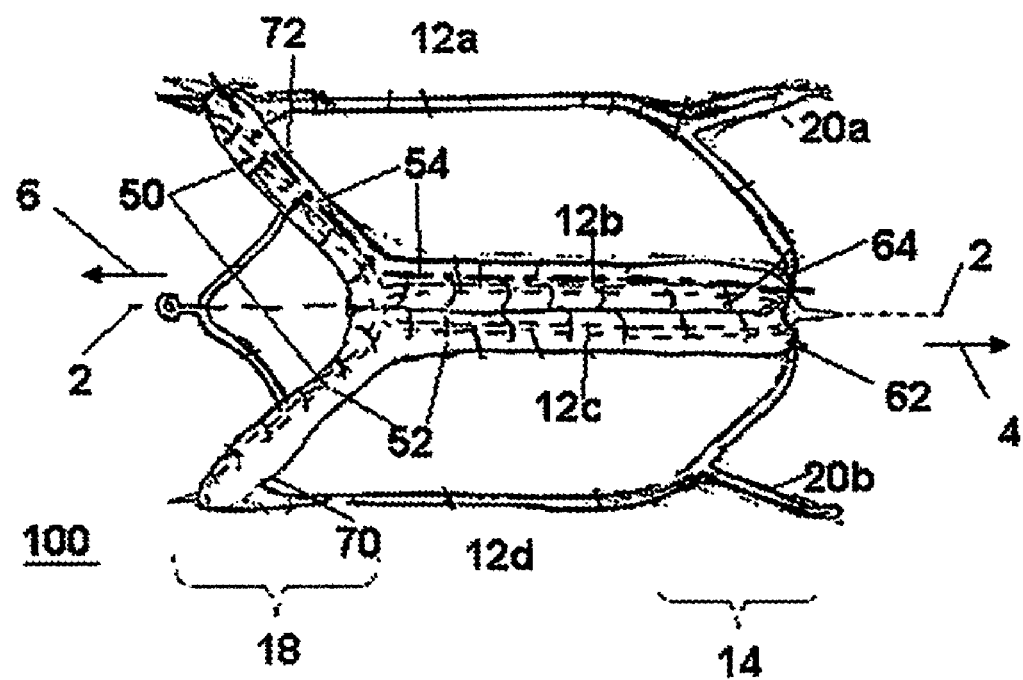
FIG. 4A is a side view of an endolumenal valve formed by attaching a pair of opposable valve leaflets to a frame comprising weakened frame portions.
Figure 4B:
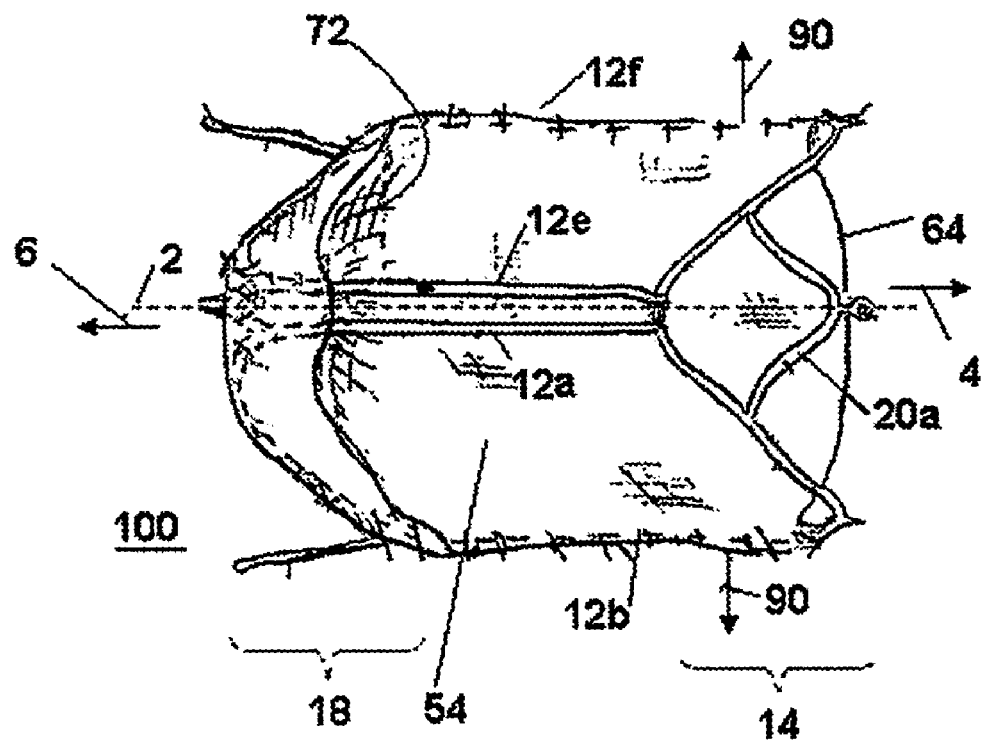
FIG. 4B is a rotated side view of the endolumenal valve shown in FIG. 4A.
Figure 4C:
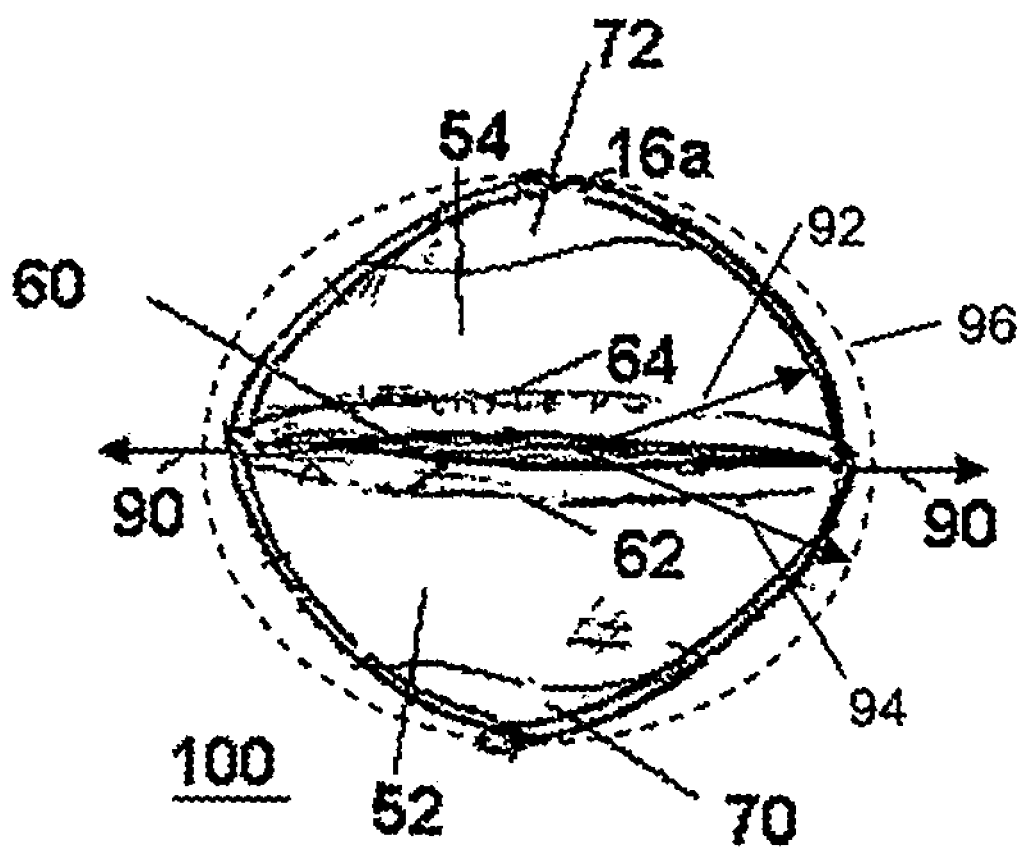
FIG. 4C is a top view of the endolumenal valve shown in FIG. 4A and FIG. 4B.
Figure 5:
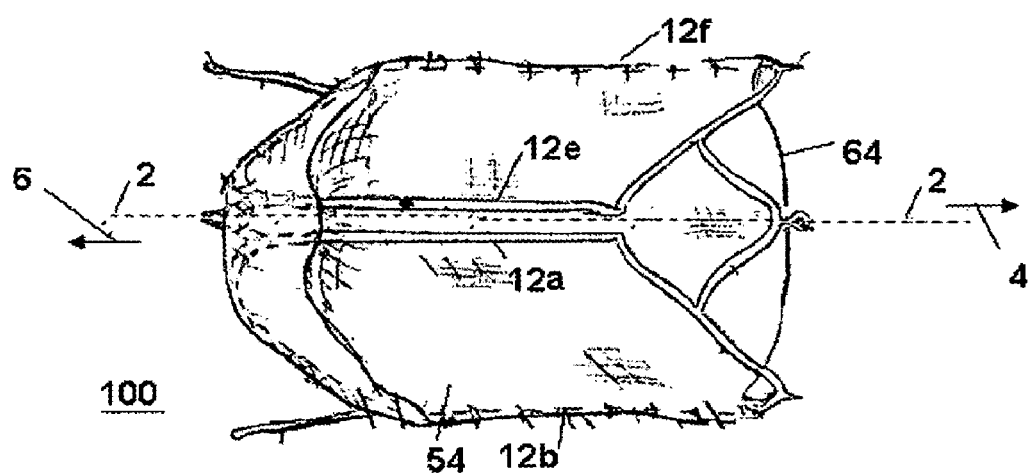
FIG. 5 is a rotated side view of a modified endolumenal valve formed by removal of the weakened frame portions shown in the endolumenal valve shown in FIGS. 4A-4C.

Preferably, medical devices comprising a frame and a valve leaflet can be used to regulate fluid flow in a vein, for example to treat venous valve incompetency. For example, one or more medical devices comprising a frame and one or more valve leaflets can be implanted in a vein with incompetent venous valves so as to provide a valve to replace the incompetent valves therein. FIG. 4A is a side view of a medical device 100 configured as a valve comprising the support frame 10 shown in FIGS. 1A-1B and a remodelable material 50. FIG. 4B is a rotated side view of the medical device 100 shown in FIG. 4A, and FIG. 4C is an top view of the medical device 100 shown in FIGS. 4A-4B. The medical device 100 is configured as an endolumenal valve by tensionably attaching two pieces of the remodelable material 50 to the frame 10 to form a first valve leaflet 54 and a second valve leaflet 52. The first valve leaflet 54 is formed by tensionably attaching the first piece of the remodelable material 50 to the strut 12b and the strut 12f. Similarly, the second valve leaflet 52 is tensionably attached between the strut 12c and strut 12g. The leaflets 52, 54 are configured to at least partially restrain the radial expansion of the self-expanding frame 10, thereby maintaining a tension on each leaflet. For example, radial expansion of the frame 10 moves struts 12b and 12f radially apart from each other, thereby providing a mechanical load on the first leaflet 54 by stretching the remodelable material of the first leaflet 54 between strut 12b and strut 12f, in a first radial direction 90 extending radially outward from, and perpendicular to, the longitudinal axis 2. Referring to FIG. 4C, the first leaflet 54 and the second leaflet 52 restrict the radial self-expansion of the frame 10. Absent the first and second leaflets 54, 52, the frame 10 would expand to a larger circular profile having a circumference indicated by dashed line 96, having a unrestrained frame lumen radius 94. Attachment of the first leaflet 54 and the second leaflet 52 reduce the frame lumen radius from the opposably to the second free edge 62. The portion of each leaflet 52, 54 distal to the free edge 62, 64 is connected to the hoop 18 to form the base of each leaflet 52, 54. Optionally, the base of each leaflet 52, 54 can be configured as a cuff forming a sinus region 70, 72 between the leaflet and the wall of a body vessel. The base of the first leaflet 52 forms a first sinus region 70, while the base of the second leaflet 54 forms a second sinus region 72. Optionally, the sinus region 70, 72 may comprise one or more holes in the leaflet material to provide for controlled fluid flow in a regrograde direction, or to drain the sinus region between pulses of fluid in the antegrade direction. FIG. 5 shows a rotated side view of the medical device 100 after weakening or removal of the weakened frame portion 16a, reducing the outward radial force of the frame 10 in the first radial direction 90, and thereby decreasing the tension of on the first valve leaflet 54 and the second valve leaflet 52.

A wide variety of materials acceptable for use as the valve leaflets are known in the art, and any suitable material can be utilized. The material chosen need only be able to perform as described herein, and be biocompatible, or able to be made biocompatible. Examples of suitable materials include flexible materials, natural materials, and synthetic materials.

A valve leaflet can optionally further comprise a suitable synthetic material including polymeric materials, such as polypropylene, expanded polytetrafluoroethylene (ePTFE), polyurethane (PU), polyethylene terphthalate (PET), silicone, latex, polyethylene, polypropylene, polycarbonate, nylon, polytetrafluoroethylene, polyimide, polyester, and mixture thereof, or other suitable materials. One preferred synthetic material comprises a polyurethane polymer and a suitable surface modifying agent, such as the biocompatible synthetic material sold under the tradename THORALON (THORATEC, Pleasanton, Calif.). Various suitable biocompatible synthetic materials comprising polyurethane, including THORALON, are described in U.S. Pat. Application Publication No. 2002/0065552 A1 and U.S. Pat. No. 4,675,361, both of which are incorporated herein by reference.

A valve leaflet can be attached to an implantable frame with any suitable attachment mechanism, such as sutures, adhesives, bonding, tissue welding, self-adhesion between regions of the material, chemical adhesion between the valve leaflet material and the frame, cross-linking and the like. The attachment mechanism chosen will depend on the nature of the frame and valve leaflets. Sutures provide an acceptable attachment mechanism when SIS or other ECM materials are used as the valve leaflets with a metal or plastic frame.

The device can include any suitable number of valve leaflets. The valve leaflets need only be able to provide the functionality described herein. The specific number chosen will depend on several factors, including the type and configuration of the frame. Some aspects provide medical devices comprising 1, 3, 4, 5, 6, 7, 8 or more valve leaflets. The valve leaflets can be arranged in any suitable configuration with respect to one another and the frame. In one preferred embodiment, a medical device can comprise a frame and three valve leaflets that are leaflets comprising free edges. In another preferred embodiment, a medical device can comprise one leaflet having a free edge that can sealably engage the interior of a vessel wall. Other suitable configurations of valve leaflets are provided by further embodiments, including differently shaped valve leaflets, and different points of attachment by valve leaflets to the frame.

In some aspects, the frame provides one or more structural features that protect a valve leaflet. For example, the frame can include a portion positioned between a portion of a leaflet and the interior wall of a body vessel upon implantation. Another example of a protecting feature in a frame includes arms or members of the frame extending between portions of a leaflet and the inner wall of a body vessel. Referring to FIG. 4A, strut 12a is positioned between the first leaflet 54 and the wall of a body vessel upon implantation of the medical device 100, and may protect the body of the first leaflet 54 from adhering to the body vessel wall. The "body" of the first valve leaflet 54 refers to the portion of the valve leaflet between the free edge 64 and the base region (sinus 72). The base of the first leaflet 54, configured as sinus region 72, is configured to form a seal with the body vessel wall, preventing fluid flow in the retrograde direction 6. Similarly, strut 12d protects the body of the second leaflet 52 from contacting the wall of a body vessel upon implantation of the medical device 100. As another example, a narrowed portion of an inner diameter of a frame around a leaflet can protect a portion of the leaflet from adhering to the inner wall of a body vessel upon implantation of a medical device therein. In one embodiment, the leaflet can comprise a remodelable material and the protecting structural feature of the frame can be bioabsorbed gradually in a time period sufficient for remodeling of at least a portion of the leaflet. Bioabsorption of the protecting feature of the frame can also gradually decrease the radial strength of the frame. In another embodiment, the protecting feature of the frame can fracture in a controlled manner, for instance by microfractures along a portion of the frame, after a suitable period of implantation (for example after about 30 days post implantation). Frames that comprise materials that decrease frame radial strength upon implantation by other means such as the absorption of fluid, responsive to changes in pH or body temperature, or various biochemical processes can also be used, for example as a structural feature to protect a leaflet or portion thereof from undesirable contact with the inner wall of a body vessel.

The overall configuration, cross-sectional area, and length of the valve support frame will depend on several factors, including the size and configuration of the device, the size and configuration of the vessel in which the device will be implanted, the extent of contact between the device and the walls of the vessel, and the amount of retrograde flow through the vessel that is desired.

In devices including multiple openings that permit a controlled amount of fluid flow in the second, opposite direction to flow through the vessel in which the device is implanted, the total open area of all openings can be optimized as described above, but it is not necessary that the individual openings have equivalent total open areas.

In one aspect, the method comprises the step of attaching a first valve leaflet to a frame. The valve leaflet can be responsive to the flow of fluid through the frame, and adapted to permit fluid flow through said vessel in a first direction or substantially prevent fluid flow through said vessel in a second, opposite direction. The frame can have a longitudinal axis, a first radial compressibility along a first radial direction that is less than a second radial compressibility along a second radial direction.

Implantable Frame Materials

Implantable frames can be constructed of any suitable material. Suitable materials are biocompatible. Preferably, the frame materials and design configurations are selected to reduce or minimize the likelihood of undesirable effects such as restenosis, corrosion, thrombosis, arrhythmias, allergic reactions, myocardial infarction, stroke, or bleeding complications. Examples of suitable materials include, without limitation: stainless steel, titanium, niobium, nickel titanium (NiTi) alloys (such as Nitinol) and other shape memory and/or superelastic materials, MP35N, gold, tantalum, platinum or platinum alloy including platinum iridium, Elgiloy, Phynox (a cobalt-based alloy), or any cobalt-chromium alloy. The stainless steel may be alloy-type: 316L SS, Special Chemistry per ASTM F138-92 or ASTM F139-92 grade 2, Special Chemistry of type 316L per ASTM F138-92 or ASTM F139-92 Stainless Steel for Surgical Implants.

A radially self-expanding frame is preferably formed partially or completely of alloys such as nitinol, which is believed to consist essentially of 55% Ni, 45% Ti, and which have superelastic (SE) characteristics. When a frame is formed from superelastic nickel-titanium (NiTi) alloys, the self-expansion occurs when the stress of compression is removed. This allows the phase transformation from martensite back to austenite to occur, and as a result the stent expands. Materials having superelastic properties generally have at least two phases: a martensitic phase, which has a relatively low tensile strength and which is stable at relatively low temperatures, and an austenitic phase, which has a relatively high tensile strength and which can be stable at temperatures higher than the martensitic phase. Shape memory alloys undergo a transition between an austenitic phase and a martensitic phase at certain temperatures. When they are deformed while in the martensitic phase, they retain this deformation as long as they remain in the same phase, but revert to their original configuration when they are heated to a transition temperature, at which time they transform to their austenitic phase. The temperatures at which these transitions occur are affected by the nature of the alloy and the condition of the material. Nickel-titanium-based alloys (NiTi), wherein the transition temperature is slightly lower than body temperature, are preferred for the present invention. It can be desirable to have the transition temperature set at just below body temperature to insure a rapid transition from the martinsitic state to the austenitic state when the frame can be implanted in a body lumen. For example, a nitinol frame can be deformed by collapsing the frame and creating stress which causes the NiTi to reversibly change to the martensitic phase. The frame can be restrained in the deformed condition inside a delivery sheath typically to facilitate the insertion into a patient's body, with such deformation causing the isothermal phase transformation. Once within the body lumen, the restraint on the frame can be removed, thereby reducing the stress thereon so that the superelastic frame returns towards its original undeformed shape through isothermal transformation back to the austenitic phase. The shape memory effect allows a nitinol structure to be deformed to facilitate its insertion into a body lumen or cavity, and then heated within the body so that the structure returns to its original, set shape.

The recovery or transition temperature may be altered by making minor variations in the composition of the metal and in processing the material. In developing the correct composition, biological temperature compatibility must be determined in order to select the correct transition temperature. In other words, when the frame can be heated, it must not be so hot that it can be incompatible with the surrounding body tissue. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979), incorporated herein by reference.

The frame may comprise one or more synthetic materials described herein, such as polyurethane synthetic materials including the polyurethane blend material sold under the tradename THORALON, as discussed herein. In other aspects, the frame may comprise a suitable biomaterial such as an ECM material, collagen, fibrin, dextran and the like.

The frame can include structural features, such as barbs, that maintain the frame in position following implantation in a body vessel. The art provides a wide variety of structural features that are acceptable for use in the medical device, and any suitable structural feature can be used. Furthermore, barbs can also comprise separate members attached to the frame by suitable attachment means, such as welding and bonding.

Also provided are embodiments wherein the frame comprises a means for orienting the frame within a body lumen. For example, the frame can comprise a marker, such as a radiopaque portion of the frame that would be seen by remote imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel. The addition of radiopacifiers (i.e., radiopaque materials) to facilitate tracking and positioning of the medical device may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film.

The frame can be manufactured by any suitable approach. In one aspect, wire struts can be formed by folding a continuous member, or be joined by soldering, welding, or other methods to join ends. In another aspect, besides joining strut segments, the frame can be fabricated as a single piece of material, by stamping or cutting the frame from another sheet (e.g., with a laser), fabricating from a mold, or some similar method of producing a unitary frame.

In yet another aspect, bioabsorbable materials can be incorporated in the frame by any suitable method, including directly fabricating the frame from the bioabsorbable material, or coating one or more bioabsorbable materials onto each other or onto another material. Bioabsorbable struts can be joined to non-bioabsorbable struts by any suitable method.

Radial Strength Measurement

The radial strength of a frame is preferably measured using a Radial Force Gauge. One preferred Radial Force Gauge the RX600 Radial Expansion Force Gage equipment from Machine Solutions Inc. (MSI). A Radial Force Gauge measures the radial strength of both balloon expandable and self-expanding stent and stent graft products during expansion and compression. The RX600 equipment uses a segmental compression mechanism controlled by a micro-stepping linear actuator that is designed to provide an extremely low friction testing environment. Preferably, the Radial Force Gauge maintains resolution at force levels from 0 to 80 Newtons, for example using a software-controlled interchangeable linear force transducer, or other suitable means. The Radial Force Gauge preferably measures the hoop strength of the frame. Optionally, the Radial Force Gauge allows the hoop strength of the frame to be visualized and recorded as the product is cycled through programmed open and close diameters.

Radial Strength Reducing Tests

The radial strength of a frame can preferably be reduced by a radial strength reducing test outside a body vessel, or by implantation within a body vessel. A radial strength reducing test refers to subjecting the frame to any environment for any time period sufficient to reduce the radial strength of the frame. Preferably, a radial strength reducing test subjects the frame to test conditions that simulate one or more conditions within a body vessel after implantation that promote the reduction in radial strength of the frame within the body vessel. In one aspect, a frame is subjected to radial strength reducing test conditions ("test conditions") of mechanical stress or a chemical environment, or combination thereof, such that a reduction in radial strength under test conditions is predictive of a reduction in radial strength upon implantation in a body vessel. Examples of test conditions include mechanical fatigue testing and biochemical reactor conditions. Preferably, a frame is initially characterized by a first radial strength measurement prior to subjecting the frame to a test condition that reduces the radial strength, and the frame is subsequently characterized by a second radial strength measurement after exposure to the test condition. Preferably, the first radial strength measurement and the second radial strength measurement are comparable. For example, both radial strength measurements can be obtained using the same a Radial Force Gauge and radial strength measurement protocol.

Figure 6A:
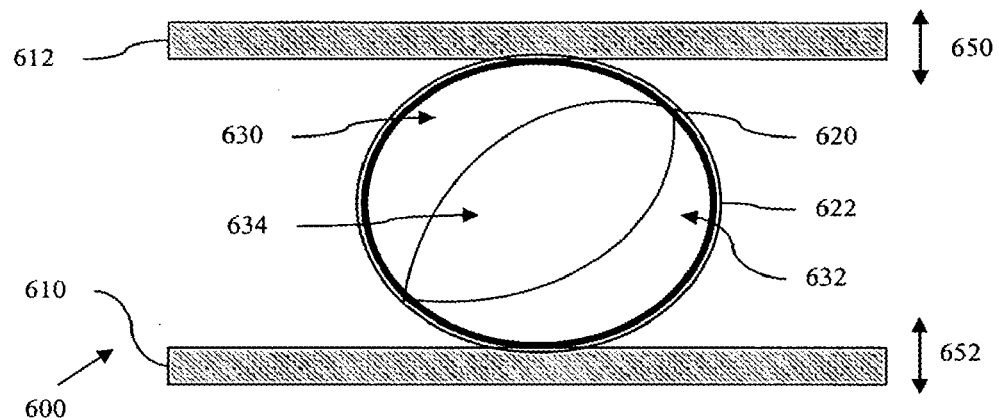
FIG. 6A is a top schematic view of a Flat Plate Fatigue Testing Apparatus and FIG. 6B is a side schematic view of the Apparatus of FIG. 6A.
Figure 6B:
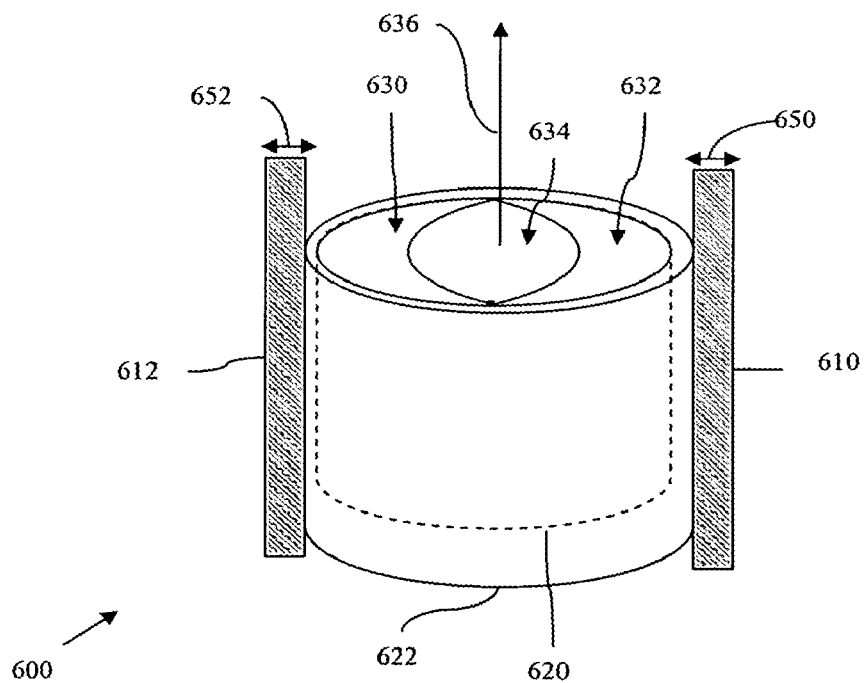

In one embodiment, the test conditions are a type of mechanical fatigue testing. For example, conditions of temperature, pressure, biochemical exposure, and mechanical loading or movement found within a body vessel can be simulated by the Flat Plate Fatigue Test. A Flat Plate Fatigue Test is a preferred mechanical fatigue test. Other mechanical fatigue tests include variations of the Flat Plate Fatigue Test. The Flat Plate Fatigue Test can be described with reference to FIG. 6A and FIG. 6B. The flat plate fatigue apparatus 600, shown schematically from a top view in FIG. 6A and a side view in FIG. 6B, comprises a first plate 610 maintained parallel to a second plate 612 that adapted to be translated in rapid oscillation with respect to each other (oscillation of the first plate 610 is indicated by arrow 652; oscillation of second plate 620 is shown by arrow 650). A tubular frame 620 has a first leaflet 630 and a second leaflet 632 attached to one end that can open to form a valve orifice 634 that opens to allow fluid flow 636 in only one direction. The tubular frame 620 is placed in a silicone tube 622, to form a frame-tube assembly that is securely positioned between the first plate 610 and the second plate 612. The flat plate fatigue apparatus 600 is positioned within a fluid-containing cell (not shown) that allows for immersing the frame 620 in a fluid. When performing the Flat Plate Fatigue Test, a fluid flow 636 of phosphate-buffered saline at about 37.degree. C. is maintained within the silicone tube 622, passing through the frame 620. The maximum distance between the first plate 610 and the second plate 612 is set to maintain each plate 610, 612 in parallel and in contact with the silicone tube 622 during the testing. During the Flat Plate Fatigue Test, the frame 620 and the silicone tube 622 are cyclically compressed between the first plate 610 and the second plate 612 for a compression of about 10% of the diameter of the uncompressed frame 620, at a rate of about 30 Hz for about 9 hours.

In other embodiments, other mechanical fatigue tests can be performed as radial strength reducing test conditions that simulate conditions within a body vessel. For example, a frame can be tested in a test similar to the Flat Plate Fatigue test, where the frame is not exposed to a fluid. Alternatively, a frame may be exposed to a fluid with certain biochemically active properties, such as the presence of enzymes. A fluid may have a particular pH range, for example to simulate pH conditions in portions of the gastrointestinal, urinary or bile tracts. The fluid may comprise whole blood or any compositions thereof, derived from any suitable source such as bovine or porcine sources. Various cycling rates may also be used, such as ranges of about 10 Hz to about 50 Hz. Also, the amount of compression of the frame may be varied, for example from about 1% to about 25% of the non-compressed diameter. The temperature of the frame or a fluid contacting the frame may be varied as well, but preferably simulates the temperature within a body vessel (about 37.degree. C. for humans). The number of oscillation cycles of the frame by movement of the flat plates can be varied to any suitable number. The number of cycles will depend on the intended use.

Frames can be designed to reduce radial strength after an intended period of time. For a frame designed to undergo a reduction in radial strength after about 6 months within a vein, about one million cycles at 30 Hz is preferred. Within the lumen of a vein in the human leg, an implanted frame is believed to undergo an estimated 5,000 oscillations per day. In one aspect, an SIS remodelable material is attached to a frame for implantation in a vein. In this environment, SIS is expected to remodel within about 6 months. Accordingly, the frame for such an application desirably loses radial strength after the number of oscillations equivalent to 6 months in a vein, or about 900,000 to one million oscillations. At an oscillation rate of about 30 Hz, the frame should undergo a reduction in radial strength after about 8.3 hours. Accordingly, the frame should have a first radial strength before the mechanical fatigue testing, and a reduced radial strength measured after about 9 hours of mechanical fatigue testing.

Frames can also be exposed to biochemical conditions that reduce the radial strength. For example, the frame can be contacted with living tissue, or placed in a bioreactor that simulates biochemical conditions within a body vessel. In one embodiment, the frame is subjected to a Blood Component Contact test, where the frame is contacted with blood for a period sufficient to reduce the radial strength of the frame, such as 30, 60, or 90 days. The blood for the Blood Contact Test can be obtained from a suitable source, such as bovine or porcine sources. Any suitable test can be used to simulate one or more conditions typically found within a body vessel where the frame is intended for implantation. For example, a frame comprising a bioabsorbable polymer can be exposed to conditions that promote the dissolution of the bioabsorbable polymer to an extent present after a desired period of implantation in a body vessel. The test conditions can be calibrated to expose the frame to conditions that cause the reduction of the frame within the body vessel, such as pH, temperature, or presence of particular bioactive blood components.

Preferably, a medical device for implantation in a body vessel comprising a frame is characterized by a first radial strength measurement prior to conducting a radial strength reducing test, and a second radial strength measurement after conducting the radial strength reducing test, where the first radial strength and the second radial strength are measured by a Radial Force Gauge; and the second radial strength measurement is less than the first radial strength measurement. More preferably, the radial strength reducing test is a Flat Plate Fatigue Test.

Delivery of Medical Devices

Medical devices are preferably delivered intralumenally, for example using various types of delivery catheters, and be expanded by any suitable mechanism. For example, a medical device can be self-expanding or non-resilient. A self-expanding medical device is restrained in a compressed configuration until deployed at a point of treatment within a body vessel by releasing the medical device. Typically, a self-expanding medical device is housed within an outer sheath of a catheter delivery system, and deployed by translating the outer sheath to expose the medical device to the body vessel at the point of deployment. In contrast, a non-resilient medical device requires the application of an internal force to expand it at the target site. Typically, the expansive force can be provided by a balloon catheter, such as an angioplasty balloon for vascular procedures.

In some aspects, a frame can expand from a compressed, or unexpanded, delivery configuration to one or more radially expanded deployment configurations, for example through self-expansion or balloon expansion of the frame. In one aspect, a medical device comprises a self-expanding material. In another aspect, a medical device is expanded using a balloon catheter. The expanded frame configuration can have any suitable cross-sectional shape, including circular or elliptical. In one embodiment, the frame can be oriented along the longitudinal axis of a body vessel in the expanded or compressed configurations.

In some embodiments, the frame is self-expanding. In one aspect, a self-expanding medical device can be compressed to a delivery configuration within a retaining sheath that is part of a delivery system, such as a catheter-based system. In some aspects, a self-expanding frame can be compressed into a low-profile delivery conformation and then constrained within a delivery system for delivery to a point of treatment in the lumen of a body vessel. Upon compression, self-expanding frames can expand toward their pre-compression geometry. At the point of treatment, the self-expanding frame can be released and allowed to subsequently expand to another configuration. In one aspect, self-expanding frames preferably have an overall expansion ratio of about 1.0 up to about 4.0 times the original diameter, or more.

In some aspects, a bioabsorbable suture or sheath can be used to maintain a medical device in a compressed configuration both prior to and after deployment. As the bioabsorbable sheath or suture is degraded by the body after deployment, the medical device can expand within the body vessel. In some embodiments, a portion of the medical device can be restrained with a bioabsorbable material and another portion allowed to expand immediately upon implantation. For example, a self-expanding frame can be partially restrained by a bioabsorbable material upon deployment and later expand as the bioabsorbable material is absorbed.

Frames can also be expanded by a balloon. A medical device can be readily delivered to the desired location by mounting it on an expandable member, such as a balloon, of a delivery catheter and passing the catheter-medical device assembly through the body lumen to the implantation site. A variety of means for securing the stents to the expandable member of the catheter for delivery to the desired location are available. It is presently preferred to compress or crimp the stent onto the unexpanded balloon. Other means to secure the stent to the balloon include providing ridges or collars on the inflatable member to restrain lateral movement, using bioabsorbable temporary adhesives, or adding a retractable sheath to cover the stent during delivery through a body lumen.

Methods for delivering a medical device as described herein are generally applicable to any suitable body vessel, such as a vein, artery, biliary duct, ureteral vessel, body passage or portion of the alimentary canal. In some embodiments, medical devices having a frame with a compressed delivery configuration with a very low profile, small collapsed diameter and great flexibility, may be able to navigate small or tortuous paths through a variety of body vessels. A low-profile medical device may also be useful in coronary arteries, carotid arteries, vascular aneurysms, and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may or may not require a sheath covering the medical device.

Methods of Treatment

The invention also provides methods of treating a patient. In one embodiment the method comprises a step of delivering a medical device as described herein to a point of treatment in a body vessel, and deploying the medical device at the point of treatment. The delivering step can comprise delivery by surgical or by percutaneous delivery techniques known to those skilled in the art. Methods for delivering a medical device as described herein to any suitable body vessel are also provided, such as a vein, artery, biliary duct, ureteral vessel, body passage or portion of the alimentary canal.

Medical devices can be deployed in a body lumen by means appropriate to their design. The medical devices of the present invention can be adapted for deployment using conventional methods known in the art and employing percutaneous translumenal catheter devices. The medical devices are designed for deployment by any of a variety of in situ expansion means.

The medical device may be mounted onto a catheter that holds the medical device as it is delivered through the body lumen and then releases the medical device and allows it to self-expand into contact with the body lumen. This deployment is effected after the medical device has been introduced percutaneously, transported translumenally and positioned at a desired location by means of the catheter. The restraining means may comprise a removable sheath. The self-expanding medical device according to the invention may be deployed according to well-known deployment techniques for self-expanding medical devices. The medical device is positioned at the distal end of a catheter with a lubricous sleeve placed over the medical device to hold the medical device in a contracted state with a relatively small diameter. The medical device may then be implanted at the point of treatment by advancing the catheter over a guidewire to the location of the lesion and then withdrawing the sleeve from over the medical device. The medical device will automatically expand and exert pressure on the wall of the blood vessel at the site of the lesion. The catheter, sleeve, and guidewire may then be removed from the patient.

For example, the tubular body of the medical device is first positioned to surround a portion of an inflatable balloon catheter. The medical device, with the balloon catheter inside is configured at a first, collapsed diameter. The medical device and the inflatable balloon are percutaneously introduced into a body lumen, following a previously positioned guidewire in an over-the-wire angioplasty catheter system, and tracked by a fluoroscope, until the balloon portion and associated medical device are positioned within the body passageway at the point where the medical device is to be placed. Thereafter, the balloon is inflated and the medical device is expanded by the balloon portion from the collapsed diameter to a second expanded diameter. After the medical device has been expanded to the desired final expanded diameter, the balloon is deflated and the catheter is withdrawn, leaving the medical device in place. The medical device may be covered by a removable sheath during delivery to protect both the medical device and the vessels.

The medical devices are useful for treating certain conditions, such as venous valve insufficiency, varicose veins, esophageal reflux, restenosis or atherosclerosis. In some embodiments, the invention relates to methods of treating venous valve-related conditions.

A "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. These venous valves open to permit the flow of fluid in the desired direction, and close upon a change in pressure, such as a transition from systole to diastole. When blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to restrict or prevent blood flow in the opposite, i.e. retrograde, direction after the pressure is relieved. The leaflets, when functioning properly, extend radially inwardly toward one another such that the tips contact each other to block backflow of blood. Two examples of venous valve-related conditions are chronic venous insufficiency and varicose veins.

In the condition of venous valve insufficiency, the valve leaflets do not function properly. For example, the vein can be too large in relation to the leaflets so that the leaflets cannot come into adequate contact to prevent backflow (primary venous valve insufficiency), or as a result of clotting within the vein that thickens the leaflets (secondary venous valve insufficiency). Incompetent venous valves can result in symptoms such as swelling and varicose veins, causing great discomfort and pain to the patient. If left untreated, venous valve insufficiency can result in excessive retrograde venous blood flow through incompetent venous valves, which can cause venous stasis ulcers of the skin and subcutaneous tissue. Venous valve insufficiency can occur, for example, in the superficial venous system, such as the saphenous veins in the leg, or in the deep venous system, such as the femoral and popliteal veins extending along the back of the knee to the groin.

The varicose vein condition consists of dilatation and tortuosity of the superficial veins of the lower limb and resulting cosmetic impairment, pain and ulceration. Primary varicose veins are the result of primary incompetence of the venous valves of the superficial venous system. Secondary varicose veins occur as the result of deep venous hypertension which has damaged the valves of the perforating veins, as well as the deep venous valves. The initial defect in primary varicose veins often involves localized incompetence of a venous valve thus allowing reflux of blood from the deep venous system to the superficial venous system. This incompetence is traditionally thought to arise at the saphenofemoral junction but may also start at the perforators. Thus, gross saphenofemoral valvular dysfunction may be present in even mild varicose veins with competent distal veins. Even in the presence of incompetent perforation, occlusion of the saphenofemoral junction usually normalizes venous pressure.

The initial defect in secondary varicose veins is often incompetence of a venous valve secondary to hypertension in the deep venous system. Since this increased pressure is manifested in the deep and perforating veins, correction of one site of incompetence could clearly be insufficient as other sites of incompetence will be prone to develop. However, repair of the deep vein valves would correct the deep venous hypertension and could potentially correct the secondary valve failure. Apart from the initial defect, the pathophysiology is similar to that of varicose veins.

While many preferred embodiments discussed herein discuss implantation of a medical device in a vein, other embodiments provide for implantation within other body vessels. In another matter of terminology there are many types of body canals, blood vessels, ducts, tubes and other body passages, and the term "vessel" is meant to include all such passages.

EXAMPLES

The tension on valve leaflet material in two implantable valves having the configuration shown in FIGS. 4A-4C was measured perpendicular to the longitudinal axis of the valve as a function of the diameter of the frame lumen. The first implantable valve (Sample 1) and the second implantable valve (Sample 2) had the same configuration, except that the scale of the Sample 1 valve was smaller than the Sample 2 valve. First, the internal lumen of the implantable frame 10 was measured without the attached valve leaflets, in the radially expanded state. Each frame had the configuration shown in FIGS. 1A-1B. Next, SIS valve leaflets were tensionably attached to to each frame 10 in the manner shown in FIGS. 4A-4C. Attachment of the valve leaflets 52, 54 restricted the radial expansion of the frame 10 and the reduced lumen diameter was measured after leaflet attachment. The tension on each SIS leaflet was measured perpendicular to the longitudinal axis 2 of each valve by subtracting the outward radial force exerted by the frame before attachment of the leaflets, and the outward radial force exerted by the frame with the SIS leaflets attached. The results of the measurements are shown in Table 1 below. TABLE-US-00001 TABLE 1 SIS Lateral Bare Frame, Tension (N) Fully Expanded Lumen Dia. With (perpendicular to Lumen Dia. Attached SIS longitudinal axis (mm) Leaflets (mm) of lumen) Sample 1 14.00 .+−. 0.25 13.0 .+−. 1.0 1.5 N Sample 2 16.50 .+−. 0.25 15.0 .+−. 1.0 3.5 N In Sample 1, attachment of the leaflets restrained the radial expansion of the frame, reducing the diameter by about 1 mm (a reduction in diameter from about 14 mm to about 13 mm, or about a 7% reduction). The valve leaflets of Sample 1 were subject to an estimated force of about 1.5 N between two struts opposably positioned across the lumen of the frame. The valve of Sample 2 was slightly larger than Sample 1, having an expanded diameter of about 16.50 mm. Attachment of the valve leaflets to the frame of Sample 2 reduced the diameter of the frame to about 15 mm, about a 9% reduction in the lumen diameter that subjected the valve leaflets to an estimated force of about 3.5 N. The leaflet preferably is subjected to a tension between attachment points located on two struts positioned opposite the valve lumen from each other.

The invention includes other embodiments within the scope of the claims, and variations of all embodiments, and is limited only by the claims made by the Applicants. Some methods further comprise the step of implanting one or more frames attached to one or more valve leaflets, as described herein. In some embodiments, methods of treating may also include the step of delivering a medical device to a point of treatment in a body vessel, or deploying a medical device at the point of treatment.

We claim:

1. An implantable medical device, comprising:
a self-expandable support frame having radially compressed and radially expanded configurations, the support frame having a perimeter that defines a lumen and comprising first, second, and third struts positioned along the perimeter, and a weakened frame portion joining the first and second struts and having a first configuration in which the support frame has a first outward radial force and a second configuration in which the support frame has a second, lesser outward radial force; and
a remodelable material having first, second and third edges, the first edge attached to the first strut and extending along the first strut to the weakened frame portion, the second edge attached to the third strut, and the third edge extending between the first and second edges and across the lumen and comprising a free edge not attached to the support frame;
wherein the remodelable material is tensionably attached to the first and third struts such that the remodlable material restricts expansion of the support frame from the radially compressed configuration to the radially expanded configuration when the weakened frame portion is in the first configuration.

2. The implantable medical device of claim 1, wherein the weakened frame portion comprises a separate frame segment attached to the first and second struts.

3. The implantable medical device of claim 2, wherein the weakened frame portion comprises a curved frame segment attached to the first strut at a first dislocating joint and attached to the second strut at a second dislocating joint.

4. The implantable medical device of claim 3, wherein one of the first and second dislocating joints comprises a biodegradable adhesive joining the curved frame segment to the first or second strut.

5. The implantable medical device of claim 3, further comprising a flexible retaining ring encircling the one of the first and second dislocating joints.

6. The implantable medical device of claim 1, wherein the weakened frame portion comprises a strut comprising a non-bioabsorbable core material surrounded by a bioabsorbable material.

7. The implantable medical device of claim 1, wherein the weakened frame portion comprises a strut comprising a non-bioabsorbable core material having an outer surface defining a series of indentations and a rigid bioabsorbable material deposited in the indentations.

8. The implantable medical device of claim 1, wherein the support frame further comprises a fourth strut positioned along the perimeter and a second weakened frame portion joining the third and fourth struts;
the second edge of the bioremodelable material attached to the third strut and extending along the third strut to the second weakened frame portion.

9. The implantable medical device of claim 1, wherein the first and third struts are positioned opposite each other relative to the lumen of the support frame.

10. The implantable medical device of claim 1, wherein the support frame comprises stainless steel.

11. The implantable medical device of claim 1, wherein the support frame comprises a nickel titanium alloy.

12. The implantable medical device of claim 1, wherein the support frame comprises a cobalt-chromium alloy.

13. The implantable medical device of claim 1, wherein the remodelable material comprises a collagenous material.

14. The implantable medical device of claim 1, wherein the remodelable material comprises an extracellular matrix material.

15. The implantable medical device of claim 14, wherein the extracellular matrix material comprises one of submucosa, renal capsule membrane, dermal collagen, dura mater, pericardium, fascia lata, serosa, peritoneum and liver basement membrane.

16. The implantable medical device of claim 14, wherein the extracellular matrix material comprises submucosa selected from the group consisting of intestinal submucosa, stomach submucosa, urinary bladder submucosa, and uterine submucosa.

17. The implantable medical device of claim 14, wherein the extracellular matrix material comprises small intestine submucosa.

18. The implantable medical device of claim 14, further comprising a non-native bioactive component incorporated into the extracellular matrix material.

19. An implantable medical device, comprising:
a self-expandable support frame having radially compressed and radially expanded configurations, the support frame having a perimeter that defines a lumen and comprising first, second, third and fourth struts positioned along the perimeter, a first weakened frame portion positioned on the perimeter and joining the first and second struts, and a second weakened frame portion positioned on the perimeter and joining the third and fourth struts, the first weakened frame portion positioned opposite the second weakened frame portion with respect to the lumen; and
a remodelable material having first, second and third edges, the first edge attached to the first strut and extending along the first strut to the weakened frame portion, the second edge attached to the third strut and extending along the third strut to the second weakened frame portion, and the third edge extending between the first and second edges and across the lumen and comprising a free edge not attached to the support frame;

wherein the first and second weakened frame portions each have a first configuration in which the support frame has a first outward radial force and a second configuration in which the support frame has a second, lesser outward radial force; and wherein the remodelable material is tensionably attached to the first and third struts such that the remodelable material restricts expansion of the support frame from the radially compressed configuration to the radially expanded configuration when the weakened frame portion is in the first configuration.

20. An implantable medical device, comprising:

a self-expandable support frame having radially compressed and radially expanded configurations, the support frame having a perimeter that defines a lumen and comprising first, second, third and fourth struts positioned along the perimeter, a first weakened frame portion positioned on the perimeter and joining the first and second struts, and a second weakened frame portion positioned on the perimeter and joining the third and fourth struts, the first weakened frame portion positioned opposite the second weakened frame portion with respect to the lumen; and a remodelable material having first, second and third edges, the first edge attached to the first strut and extending along the first strut to the weakened frame portion, the second edge attached to the third strut and extending along the third strut to the second weakened frame portion, and the third edge extending between the first and second edges and across the lumen and comprising a free edge not attached to the support frame;

wherein the first and second weakened frame portions each have a first configuration in which the support frame has a first outward radial force and a second configuration in which the support frame has a second, lesser outward radial force;

wherein the first weakened frame portion comprises a first curved frame segment attached to the first strut at a first dislocating joint and attached to the second strut at a second dislocating joint and the second weakened frame portion comprises a second curved frame segment attached to the third strut at a third dislocating joint and attached to the fourth strut at a fourth dislocating joint; and wherein the remodelable material is tensionably attached to the first and third struts such that the remodelable material restricts expansion of the support frame from the radially compressed configuration to the radially expanded configuration when the weakened frame portion is in the first configuration.

* * * * *